(12) United States Patent
Uenishi et al.

(10) Patent No.: US 7,432,381 B2
(45) Date of Patent: Oct. 7, 2008

(54) 1,3-OXATHIOLANE-2-THIONE COMPOUNDS

(75) Inventors: Kazuya Uenishi, Nara (JP); Atsushi Sudo, Tokyo (JP); Hiroshi Morikawa, Uki (JP); Takeshi Endo, Yokohama (JP); Olaf Lammerschop, Krefeld (DE); Thomas Huver, Duesseldorf (DE); Pavel Gentschev, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 11/354,390

(22) Filed: Feb. 15, 2006

(65) Prior Publication Data

US 2006/0293280 A1 Dec. 28, 2006

Related U.S. Application Data

(63) Continuation of application No. PCT/EP2004/008932, filed on Aug. 10, 2004.

(30) Foreign Application Priority Data

Aug. 15, 2003 (EP) .................................. 03018504
Apr. 5, 2004 (WO) ................ PCT/EP2004/003602

(51) Int. Cl.
*C07D 327/04* (2006.01)
(52) U.S. Cl. ................... 549/4; 549/30; 549/62; 549/214; 549/313
(58) Field of Classification Search .......... 549/4, 549/30, 62, 214, 313
See application file for complete search history.

(56) References Cited

U.S. PATENT DOCUMENTS

| | | | |
|---|---|---|---|
| 3,278,484 A | 10/1966 | Tesoro | |
| 3,700,715 A | 10/1972 | Berger | |
| 5,701,443 A | 12/1997 | Oguma et al. | |
| 5,789,085 A | 8/1998 | Blohowiak et al. | |
| 5,792,881 A | 8/1998 | Wolter et al. | |
| 5,849,110 A | 12/1998 | Blohowiak et al. | |

FOREIGN PATENT DOCUMENTS

| | | | |
|---|---|---|---|
| EP | 0 943 660 A1 | | 9/1999 |
| JP | 11 191117 | | 7/1999 |
| JP | 11 246632 | | 9/1999 |
| JP | 11-246632 | * | 9/1999 |
| JP | 2002 47424 | | 2/2002 |
| WO | WO 97/02270 A1 | | 1/1997 |

OTHER PUBLICATIONS

Uenishi et al. Abstract of Heteroatom Chemistry (1995), 6(4), p. 325-32 from STN search results.*

Uenishi et al., Journal of Chemical Society, Chemical Communications, 1991, vol. 20, p. 1421-2.*

Patent Abstracts of Japan, vol. 2002, No. 06 for JP2002 47424 (Jun. 2002).

Patent Abstracts of Japan, vol. 1999, No. 14 for JP 11 246632 (Dec. 1999).

Choi et al., "A Novel Construction of Living Polymerization by Neighboring Group Participation: Living Cationic Ring-Opening Polymerization of a Five-membered Cyclic Dithiocarbonate", *Macromolecules*, American Chemical Society, Easton, US, vol. 31, No. 25, pp. 9093-9095, XP000788852, ISSN: 9924-9297 (Dec. 1998).

Takeshi Moriguchi et al., "Polyaddition of Bifunctional Dithiocarbonates Derived from Epoxidesand Carbon Disulfide Synthesis of Novel Poly(thiourethanes)", Macromolecules, American Chemical Society Easton, US, vol. 28, No. 15, pp. 5386-5387, XP000515368, ISSN: 0024-9297 (Jul. 1995).

* cited by examiner

*Primary Examiner*—Joseph McKane
*Assistant Examiner*—Yong Chu
(74) *Attorney, Agent, or Firm*—Dilworth & Barrese, LLP

(57) ABSTRACT

The present invention relates to 1,3-oxathiolane-2-thione compounds of the general formula (I):

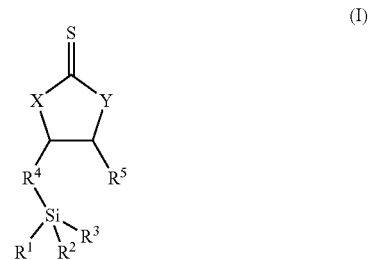

wherein $R^1$ and $R^2$ are the same or different, each of which denotes a straight-chain or branched alkoxy residue with 1 to 6 carbon atoms or an aryloxy or aralkyloxy residue, $R^3$ is different or the same as $R^1$ or $R^2$ or an aliphatic residue, an amino residue, a halogen residue, an aromatic or heteroaromatic residue, or an aralphatic or heteroaralphatic residue, $R^4$ is a bridging group selected from the groups consisting of aliphatic, heteroaliphatic, aralphatic, heteroaralphatic, aromatic and heteroaromatic groups and $R^5$ is hydrogen, an aliphatic, heteroaliphatic, aralphatic, heteroaralphatic, aromatic, heteroaromatic, cycloaliphatic or heterocycloaliphatic group or $R^4$ and $R^5$ form a cycloaliphatic, cycloheteroaliphatic, aromatic or heteroaromatic residue, which is optionally substituted with an aliphatic, heteroaliphatic residue serving as a bridging group to the silicon atom and X and Y are different and selected from oxygen and sulfur and mixtures of such compounds.

4 Claims, No Drawings

1,3-OXATHIOLANE-2-THIONE COMPOUNDS

CROSS-REFERENCE TO RELATED APPLICATIONS

This application is a continuation under 35 USC Sections 365(c) and 120 of International Application No. PCT/EP2004/008932, filed 10 Aug. 2004 and published in English 24 Feb. 2005 as WO 2005/016939, which claims priority from International Application No. PCT/EP04/003602, filed 5 Apr. 2004 and published in English 24 Feb. 2005 as WO 2005/016995, and European Application No. 03018504.5, filed 15 Aug. 2003, each of which is incorporated herein by reference in its entirety.

FIELD OF THE INVENTION

The present invention relates to a novel class of 1,3-oxathiolane-2-thione key intermediate compounds and compounds produced therefrom, a method of the manufacture of the novel 1,3-oxathiolane-2-thiones and their use as and in coatings, sealants, primers and adhesion promoters for coating and bonding of various metallic and non-metallic materials.

DISCUSSION OF THE RELATED ART

There is a big need to provide surfaces with primers and other coatings to equip the substrate with anti-corrosive and moisture insensitive characteristics as well as enhanced adhesion properties. Moreover, compounds are needed to act as adhesion promoters and adhesive agents showing an excellent curability combined with a multitude of modification possibilities to ensure selective binding of molecules to such surfaces in a chemical or physical manner. Several approaches have been made to provide compounds serving as potent candidates for the above purposes. Nevertheless, the state of the art compounds do not combine all desired features as some of them are moisture sensitive, lack the possibility of being capable of modification and therefore customized easily or suffer from drawbacks like high volume shrinkage and the like.

Japanese Patent Application No. 1999-191117 discloses primers containing heterocyclic oxathiolanethione derivatives, m-xylylenediamine, epoxy resins and neopentyl glycol diglycidyl ether, in particular for use in concrete production. Anticorrosive coating compositions with similar ingredients are described in Japanese Patent Application No. 1999-372469.

Japanese Patent Application No. 2000-234080 discloses rapidly curable, storage stable resin compositions comprising dithiocarbonates and oxazolidines and/or ketimines.

Low-temperature-curable epoxy resin compositions are reported in Japanese Patent Application No. 2001-259110. The therein disclosed compositions comprise oxathiolanethione derivatives, polysulfide-modified epoxy resins and compounds with at least two active hydrogen atoms from amino groups.

Further epoxy resin compositions containing dithiocarbonates are described in Japanese Published Patent Application No. 2000-273150-A for use in fiber reinforced composite material and in Japanese Published Patent Application No. 2001-206934-A for use in anticorrosion coatings, exterior and car coatings, powder coatings, as primers and structural adhesives.

None of the documents discussed above describes compounds containing a dithiocarbonate group and a further reactive group, like, e.g., a silyl group within one molecule.

Japanese Patent Publication No. 11-246632 concerns polymeric compounds for use in paints, adhesives, inks and sealing agents, which are prepared by copolymerization of five-membered cyclic dithiocarbonates and silanes, both carrying vinyl groups as reactive groups for polymerization. The aim of JP 11-246632 is to provide surface coatings with improved hardness, as well as water and chemical resistance. Nevertheless, these molecules are polymeric and limited in their ability to be selectively modified compared to single monomeric units.

BRIEF SUMMARY OF THE INVENTION

One object of the present invention is to overcome the problems of the prior art compounds and to provide key intermediates that are suitable as adhesion promoters with improved volume shrinkage characteristics, enhanced corrosion resistance properties and enhanced curing abilities, the latter one being due to the presence of different crosslinking groups such as thiol or siloxy groups within one molecule.

A further object of the invention is to provide compounds that can be applied to a large variety of different surface materials before or after selective modification by reaction to form multi-crosslinked or multi-crosslinkable coatings or primers, that are free of chromium compounds.

The compounds should also be curable or crosslinkable by so-called sol-gel formation. Such sol-gels should be able to adhere or chemically bind to metallic and non-metallic surfaces and to provide for enhanced adhesion of further adhesives to be applied. Application areas should range from treatment of surfaces such as glass and silicon wafers to metal and alloy bonding purposes or aircraft paintwork. Moreover, compounds should be provided that are useful in universal applications concerning surface (pre)-treatment, coating and bonding as well as adhesion promoting.

The above problems have been solved by providing a novel class of 1,3-oxathiolane-2-thione compounds (siloxy group coupled cyclic dithiocarbonates; hereinafter referred to as cycDTC-Si) having the following general formula (I):

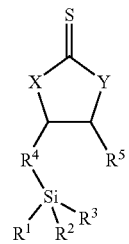

wherein:
$R^1$ and $R^2$ are the same or different, each of which denotes a straight-chain or branched alkoxy residue with 1 to 6 carbon atoms or an aryloxy or aralkyloxy residue;
$R^3$ is different or the same as $R^1$ or $R^2$ or an aliphatic residue, an amino residue, a halogen residue, an aromatic or heteroaromatic residue, an araliphatic or heteroaraliphatic residue or consists of one or more siloxy groups;
$R^4$ is a bridging group selected from the groups consisting of aliphatic, heteroaliphatic, araliphatic, heteroaraliphatic, aromatic and heteroaromatic groups;
$R^5$ is hydrogen, an aliphatic, heteroaliphatic, araliphatic, heteroaraliphatic, aromatic, heteroaromatic, cycloaliphatic or heterocycloaliphatic group or
$R^4$ and $R^5$ form a cycloaliphatic, cycloheteroaliphatic, aromatic or heteroaromatic residue, which is optionally substituted with an aliphatic, heteroaliphatic residue serving as a bridging group to the silicon atom; and X and Y are different and selected from oxygen and sulfur, and mixtures of such compounds.

DETAILED DESCRIPTION OF CERTAIN EMBODIMENTS OF THE INVENTION

It is preferred that the compounds of the above general formula (I) contain a trialkoxysilyl group, i.e., that $R^1$, $R^2$ and $R^3$ are the same or different and each of them is a straight-chain or branched alkoxy residue with 1 to 4 carbon atoms. Even more preferred are the compounds wherein $R^1$, $R^2$ and $R^3$ are the same or different and wherein each denotes a methoxy or ethoxy residue.

The preference for trialkoxysilyl groups instead of dialkoxymonoalkylsilyl groups is due to the increased ability to form sol-gels when using trialkoxysilyl groups.

Methoxy and ethoxy residues are preferred because of the ready commercial availability of such precursor compounds. Nevertheless, further practical reasons account for the use of compounds with methoxy and ethoxy residues. In view of the sol-gel formation, pot life is one crucial issue for applicability during the coating process. If, e.g., a longer pot life is desired ethoxy or even propoxy residues are preferred over methoxy residues.

The $R^4$ group serves as a bridging group between the silyl group and the cyclic dithiocarbonate group. The choice of this group is not crucial for the function of the compounds of this invention. Therefore a wide variety of residues ranging from saturated to unsaturated, straight-chain or branched residues or aromatic residues, optionally containing hetero atoms can be part of the bridging group. In general, but not limited thereto, the bridging group contains 1 to 12 atoms standing in series between the silyl and the cyclic dithiocarbonate group. One preferable meaning of $R^4$ is —$(CH_2)_3OCH_2$— when $R^5$ is hydrogen.

$R^4$ can also form a ring system together with $R^5$. If a ring system is formed between $R^4$ and $R^5$, usually 4 to 8 atoms are involved in the ring. If, e.g., a 6-membered cycloalkyl ring is formed, the 1,3-oxathiolane-2-thione residue develops to a 1,3-benzoxathiole-2-thione residue at which the silyl residue can either be bound directly or via another spacer as in 2-{3,4-(1,3-oxathiolane-2-thionyl)cyclohexyl}-ethyltriethoxysilane or 2-{4,5-(1,3-oxathiolane-2-thionyl)cyclohexyl}ethyltriethoxy-silane (see Examples; compounds 1c and 1c'), i.e., $R^4$ and $R^5$ together form —$(CH_2$—$CH_2$—$CHR^x$—$CH_2)$— whereby $R^x$ is —$CH_2$—$CH_2$—.

The present invention further provides a method for preparation of the 5-membered cycDTC-Si. Various cycDTC-Si compounds can be synthesized by cycloaddition of carbon disulfide with epoxy-silanes according to Scheme 1:

Scheme 1

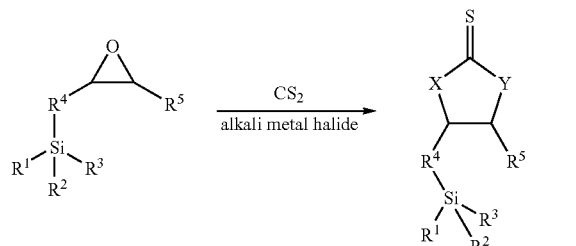

X, Y = S or O; and X not Y

In other words, the present invention provides a method for the preparation of compounds having the general formula (I):

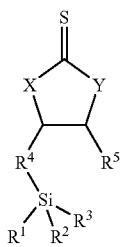

(I)

wherein
$R^1$ and $R^2$ are the same or different, each of which denotes a straight-chain or branched alkoxy residue with 1 to 6 carbon atoms or an aryloxy or aralkyloxy residue,
$R^3$ is different or the same as $R^1$ or $R^2$ or an aliphatic residue, an amino residue, a halogen residue, an aromatic or heteroaromatic residue, or an araliphatic or heteroaraliphatic residue,
$R^4$ is a bridging group selected from the groups consisting of aliphatic, heteroaliphatic, araliphatic, heteroaraliphatic, aromatic and heteroaromatic groups and
$R^5$ is hydrogen, an aliphatic, heteroaliphatic, araliphatic, heteroaraliphatic, aromatic, heteroaromatic, cycloaliphatic or heterocycloaliphatic group or
$R_4$ and $R_5$ form a cycloaliphatic, cycloheteroaliphatic, aromatic or heteroaromatic residue, which is optionally substituted with an aliphatic, heteroaliphatic residue serving as a bridging group to the silicon atom and
X and Y are different and selected from oxygen and sulfur, wherein an epoxy compound of general formula (II):

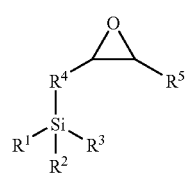

(II)

where $R^1$, $R^2$, $R^3$, $R^4$ and $R^5$ are the same as in formula (I), is brought to reaction with carbon disulfide in the presence of a catalyst.

The position at which the mandatory atoms S and O are present in the 5-membered ring (the X or Y position, respectively) depends on a variety of factors like the substitution pattern at positions 4 and 5 of the 5-membered ring, the choice of catalyst, reaction conditions like temperature and the like. Nevertheless, for fulfillment of the uses of the invention both isomers are suitable.

As a catalyst, various alkali metal halides, such as chlorides, iodides and bromides of sodium, potassium and lithium can be used. Most commonly used are the iodides and bromides of sodium and lithium, whereby the most preferable one is lithium bromide in view of selectivity and yield when an ether, such as the cyclic ether tetrahydrofuran, is used as a solvent. Further examples are lithium chloride, lithium iodide, sodium chloride, sodium bromide, sodium iodide, potassium chloride, potassium bromide and potassium iodide. Other catalysts that might be employed include, e.g., oxides like aluminum oxides, titanium oxides, silica, tin oxide, zinc oxide and lead(II)oxide.

The reaction can be preformed with or without solvents. As reaction media, various solvents can be used instead of or in combination with ethers or cyclic ethers like tetrahydrofuran. Possible solvents are, e.g., ketones such as acetone or ethylmethylketone, amides such as dimethylformamide and N-methylpyrrolidin-2-one, alcohols such as methanol, ethanol, and 2-propanol, nitrites such as acetonitrile and propionitrile, as well as solvent mixtures.

The reaction is preferably performed at a temperature of 0 to 100° C. and a pressure of 1 to 5 atmospheres. More preferably, the reaction is carried out at a temperature of 0 to 50° C. and a pressure of 1 to 2 atmospheres. The silyl group is not affected under the reaction conditions.

The compounds of the present invention are in particular useful in pre-treatment, surface coating and bonding of various metallic and non-metallic surfaces, including surfaces like aluminum, titanium, steel, gold, silver, copper, various alloys, glass, and silicon in any shape from macroscopically flat surfaces to small particles.

The compounds of the present invention can easily form a solvent-resistant layer on surfaces of various materials by sol-gel reaction of the silyl part, whereby a combination with other silyl compounds is possible (see Scheme 2). The conditions for sol-gel reactions are known to the skilled in the art and not deemed to limit the scope of the present invention. Usually such reactions are acid or base induced. Most commonly used acids and bases used for sol-gel formation are inorganic acids such as hydrochloric acid and sulfuric acid, organic acids such as acetic acid and p-toluenesulfonic acid, inorganic bases such as sodium hydroxide, potassium hydroxide, and ammonia, and organic bases such as amines. Moreover, U.S. Pat. Nos. 5,849,110 and 5,789,085, each of which is incorporated herein by reference in its entirety, describe several possible mechanisms of sol-gel formation of epoxy-silanes.

When reactive groups such as hydroxy groups, amino groups, carboxy groups, thiol groups and the like are present on the surface to be treated, the layer can be covalently bound to the surface.

Scheme 2

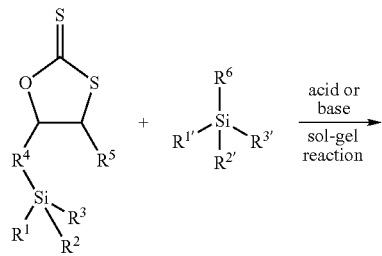

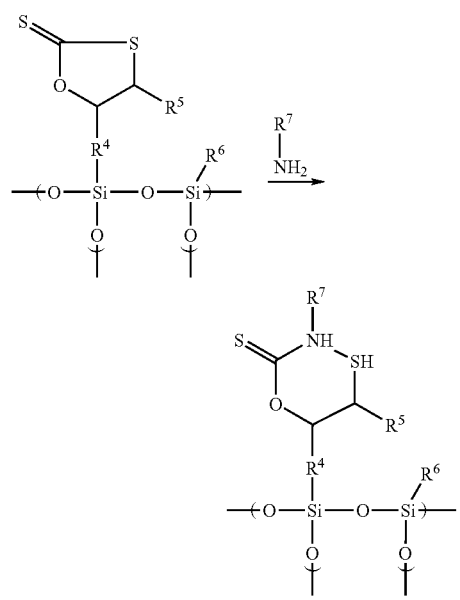

Thus pre-treated (or coated) surfaces have the following features:

The pre-treated (or coated) substrate bears cyclic dithiocarbonates (cycDTC) on its surface, which can react with amines in adhesive formulations (Scheme 3). By this ring cleavage reaction, thiol groups are formed. The thiol groups can further react with epoxides in the adhesive formulation. These reactions improve the resulting adhesion performance. In addition, on the pre-treated (or coated) surface, various peptides, nucleic acids, and other functional molecules can be immobilized by their reactions with cycDTC. Due to the very selective reaction of cycDTC with amines, the modified surface is relatively moisture inert or insensitive and therefore has an enhanced long-term stability compared to the conventional ones bearing epoxide and isocyanate groups at the surface.

Scheme 3

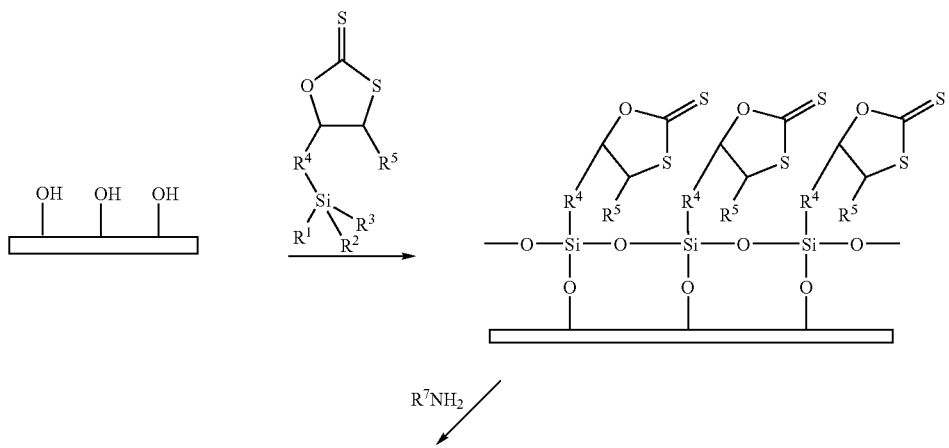

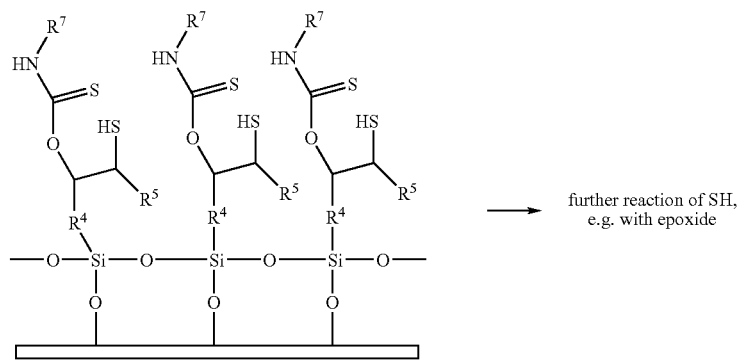

Using photo-latent amines, photo-patterning can be achieved on the pre-treated surface (Scheme 4). Examples of such photo-latent amines are O-acyloximes (cf. JP2002-201256). The patterned reactive surface can afterwards, e.g., be used to immobilize peptides and enzymes by the oxidative coupling of their thiol groups with the thiol group of the surface.

The surface thiol group can be also used for immobilization of various metal nano-particles such as gold, silver or copper, and the immobilized particles can form nano-scale circuits for nano-size electronic devices.

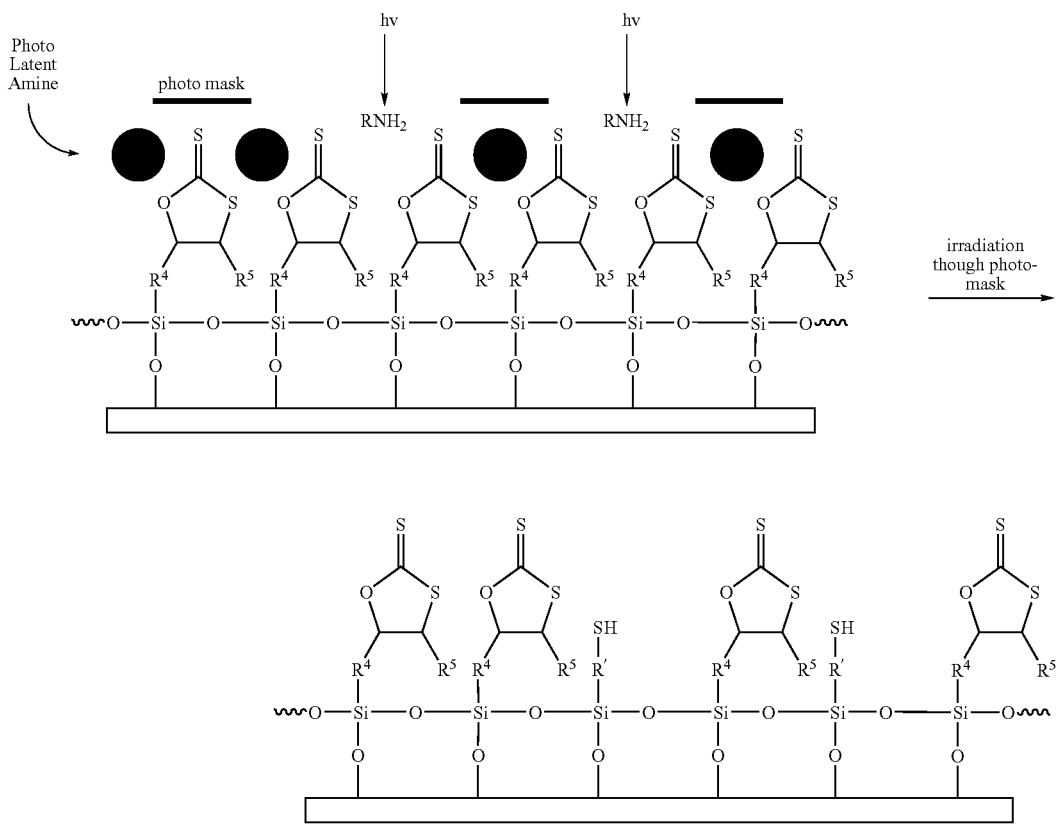

Moreover, the pre-treated surfaces of particles (e.g., silica-gel particles, metal particles, and other organic and inorganic particles) bearing cycDTC, can react with amines in adhesive and sealant formulations (Scheme 5). This reaction forms covalent bonds between the surface and adhesives and sealants to improve the adhesion performance, properties of adhesives and those of sealants. The particles can be used as scavengers for amines. In addition, the particles can be modified by reaction with amines, and appropriately modified ones can be used as stationary phases for column chromatography.

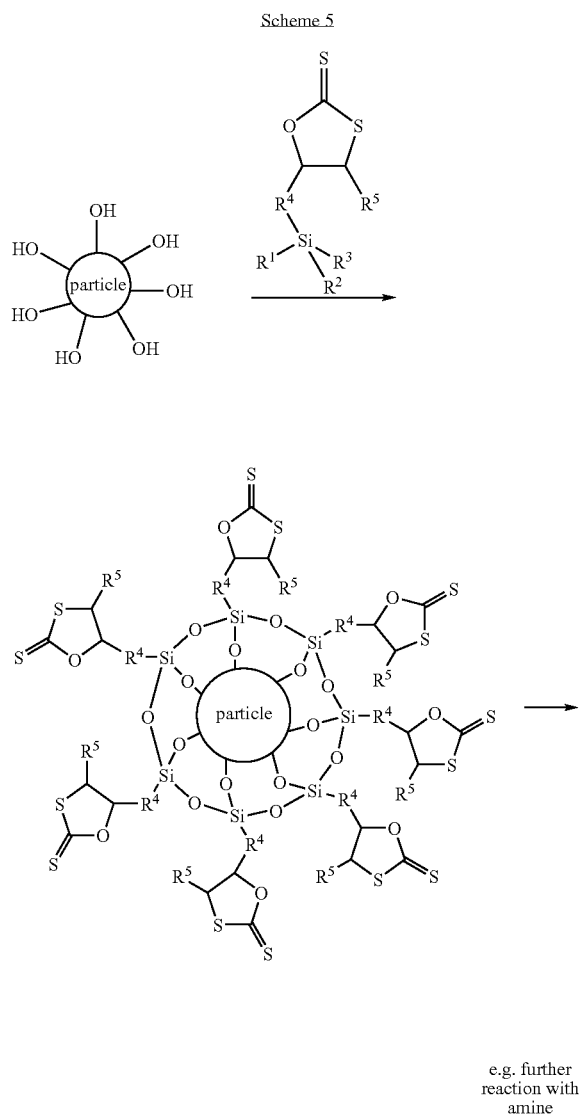

e.g. further reaction with amine

Another field of application makes use of liquid oligosiloxanes, crosslinked polysiloxanes, and linear polysiloxanes bearing the cycDTC group (Scheme 6). The siloxane part of cycDTC-Si polymerizes (acid or base catalyzed) in a sol-gel reaction in the presence of moisture. As catalysts, various acidic and basic reagents, which are commonly used for sol-gel reaction can be employed. Co-polymerization with other siloxanes is also possible (Scheme 6), nevertheless the siloxanes described in Scheme 6 can also be omitted.

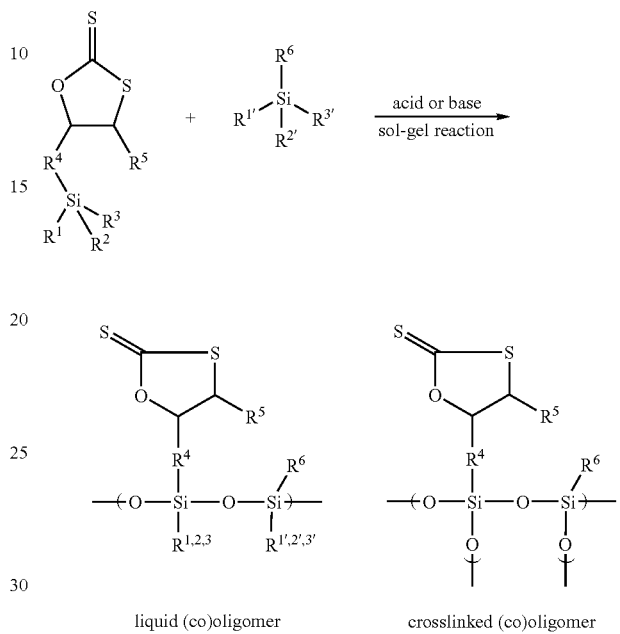

liquid (co)oligomer
or
linear (co)polymer crosslinked (co)oligomer

The crosslinked (co)oligomer is a solid (monolith or powder) and insoluble in any solvent. The cycDTC part of it can react with amines as described above. Based on this reaction, the crosslinked (co)oligomer has the same features as the surface bound analogues discussed for the pre-treatment (or coating) of materials.

If the above reaction is carried out in the presence of compounds of the general formula $SiR^{1'}R^{2'}R^{3'}R^6$, the residues would preferably denote as follows:

$R^{1'}$ and $R^{2'}$ are the same or different, each of which denotes a straight-chain or branched alkoxy residue with 1 to 6 carbon atoms or an aryloxy or aralkyloxy residue;

$R^{3'}$ is different or the same as $R^1$ or $R^2$ or an aliphatic residue, an amino residue, a halogen residue, an aromatic or heteroaromatic residue, or an araliphatic or heteroaraliphatic residue; and $R^6$ denotes a straight-chain or branched aliphatic, heteroaliphatic, araliphatic, heteroaraliphatic, aromatic or heteroaromatic group.

By variation of the reaction time, it is possible to selectively obtain liquid and solid products, respectively. A short reaction time in general leads to liquid products and longer reaction times give solid products. In most cases, but always depending on the starting materials, a 5 hour reaction time leads to a liquid product. To the contrary, reaction times of, e.g., more than 24 hours are employed if solid products are desired to be obtained.

The liquid (co)oligomers are less volatile than monomeric cycDTC, and have higher viscosity, and therefore can be handled more easily than monomeric cycDTC. The obtained liquid (co)oligomers are soluble in organic solvents and are miscible with various organic compounds.

Treatment of the liquid (co)oligomers with amine results in a ring opening reaction of the cycDTC moiety in the side chain of the oligomers and post condensation reactions of the oligosiloxane part to give crosslinked polysiloxanes (Scheme 7). Thus, the oligomers can be applied as curable materials to adhesives, coatings, and sealants.

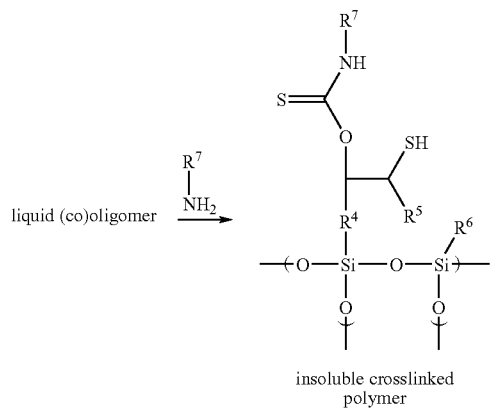

Scheme 7

The liquid (co)oligomers are miscible with epoxy resins and thus can be used in addition to epoxy resins. Using the (co)oligomers as additives for an epoxy-amine curing reaction (Scheme 8), volume shrinkage can be reduced. Addition of monomeric cycDTC-Si itself is also possible.

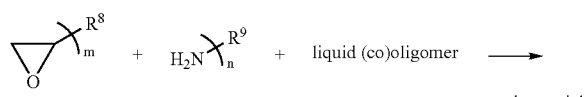

Scheme 8

Further, it is possible to prepare a monomeric thiol having a siloxy moiety by reaction of an amine with cycDTC-Si (Scheme 9). The cycDTC group of cycDTC-Si reacts with an amine of the formula $NHR^7R^{7'}$ or a polymeric polyamine selectively to give the corresponding thiourethane having thiol and siloxy moieties (the definition of $R^1$, $R^2$, $R^3$, $R^4$ and $R^5$ is as used above; and $R^7$ and $R^{7'}$ are the same or different and denote hydrogen, a straight-chain or branched aliphatic, heteroaliphatic, araliphatic, heteroaraliphatic, aromatic or heteroaromatic group). In case a polymeric polyamine is used, such as, e.g., polyoxyalkylene diamines or triamines, polymeric polyamines with a number-average molecular weight of 200 to 5000 or preferably 200 to 1000 are suitable.

By such reactions, various amines can be modified into the corresponding thiols having siloxy moieties. The thiol moiety of the adduct can, e.g., be used for oxidative coupling reactions and reactions with epoxide, similar to the other thiols as described above.

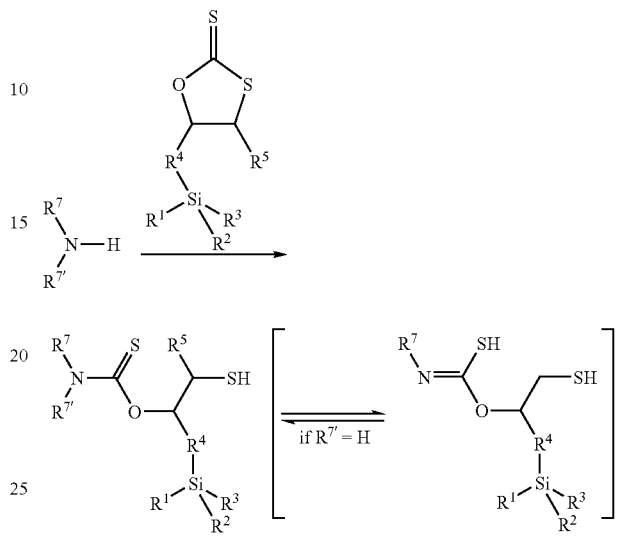

Scheme 9

The thus modified amines can be used for pre-treatment and coating of surfaces of various materials by sol-gel reaction of the siloxy group. The resulting coating layer has thiol groups, which can, e.g., react with epoxides, isocyanates, isothiocyanates, thiols, and carboxylic acid derivatives, improving adhesion performance. The physical properties of the coating layer can be controlled by choosing the starting amine.

Furthermore, the modified amine can be used as a curable material. Sol-gel reaction of the siloxy part and oxidative coupling of the thiol group results in a strong curing reaction with a high degree of crosslinking.

Another use of such modified amines is the use as a curing reagent for epoxy and urethane adhesives, coatings, and sealants. The siloxy part enhances adhesion performance and increases mechanical strength of the cured material. The thiol group promises rapid curing reaction.

Further suitable amines which can be used in the reaction as described in Scheme 9 are primary or secondary diamines having the general structure R'HN-A-NHR", wherein R' and R" independently denote hydrogen or an aliphatic, heteroaliphatic, cycloaliphatic, heterocycloaliphatic, aromatic or heteroaromatic residue or build together an alkylene residue, like —$CH_2CH_2$—, and A being an aliphatic, heteroaliphatic, cycloaliphatic, heterocycloaliphatic, aromatic or heteroaromatic residue. Such diamines can be used to cleave two cyclic dithiocarbonate compounds, as shown in Scheme 10. In particular aliphatic diamines are preferable, wherein A is a straight-chain or branched alkylene chain with 2 to 20 carbon atoms, optionally containing one or more heteroatoms, like oxygen or sulfur; or cycloaliphatic diamines, whereby the amino function NH is contained in the cycloaliphatic residue. Residues R' and R" are preferably aliphatic or heteroaliphatic groups containing 1 to 18 carbon atoms, more preferably straight-chain or branched alkyl groups containing 1 to 6 carbon atoms, optionally containing one or more heteroatoms. Examples for diamines are, e.g., given in the Table A below.

The resulting thiol groups can be further reacted by any of the above mentioned thio group reactive compounds. The reaction with isocyanates and/or isothiocyanates, in particular monoisocyanates and/or monoisothiocyanates of the general formula B'—NCX (X=S or O) and diisocyanates and/or diisothiocyanates of the general formula XCN—B—NCX (X=S or O) is preferred and also shown in Scheme 10.

diphenyldimethyl-methane diisocyanate, di- and tetraalkylene diphenylmethane diisocyanate, 4,4'-dibenzyldiisocyanate, 1,3-phenylene diisocyanate, 1,4-phenylene diisocyanate, the isomers of toluylene diisocyanates (TDI), 1-methyl-2,4-diisocyanato-cyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane

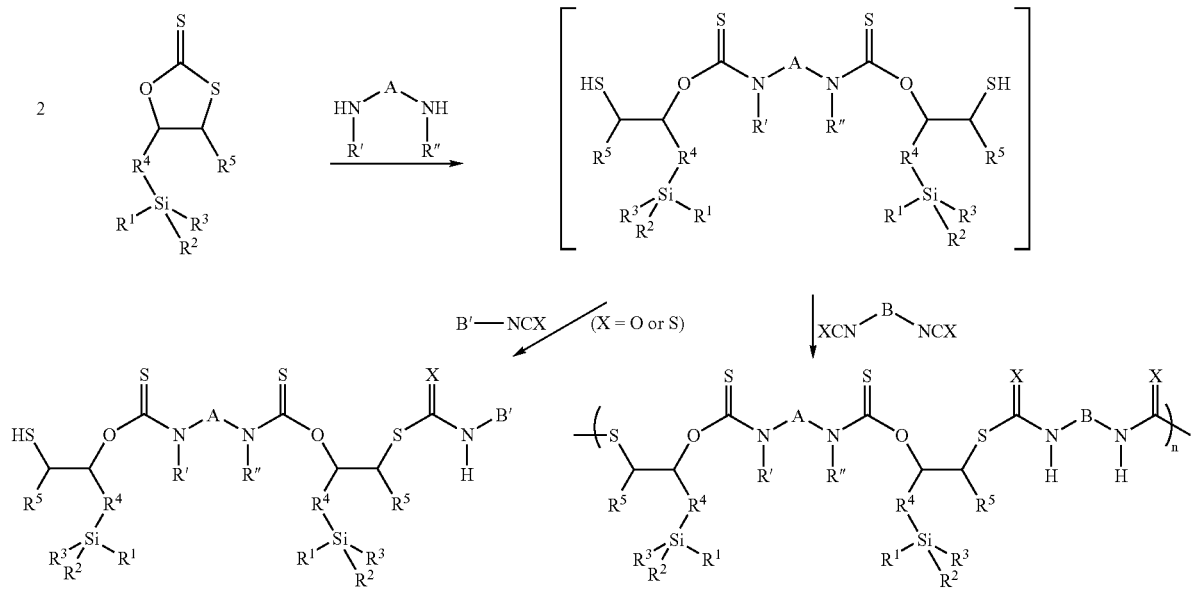

Scheme 10

Suitable representatives for monoisocyanates of the general formula B'—NCO are, preferably, aromatic monoisocyanates, such as phenyl isocyanate, tolyl isocyanate and naphthylene isocyanate. But in general the monoisocyanates are not limited to aromatic monoisocyanates and can comprise, aliphatic, heteroaliphatic, cycloaliphatic, heterocycloaliphatic, aralyphatic or heteroaralyphatic groups. Suitable representatives for monoisothiocyanates are the thio analogues of the respective monoisocyanates.

The diisocyanates and diisothiocyantates used in the above reaction are compounds having the general structure XCN—B—NCX (X=S or O), wherein B is preferably an aliphatic, alicyclic or aromatic residue, in particular an alicyclic or aromatic residue with 4 to 18 carbon atoms.

Most suitable diisocyanates are, e.g., 1,5-naphthylene diisocyanate, 2,4- or 4,4'-diphenylmethane diisocyanate (MDI), hydrogenated MDI (H12MDI), xylylene diisocyanate (XDI), tetramethylxylylene diisocyanate (TMXDI), 4,4'-(IPDI), tetramethoxybutane-1,4-diisocyanate, butane-1,4-diisocyanate, hexane-1,6-diisocyanate (HDI), dicyclohexylmethane diisocyanate, cyclohexane-1,4-diisocyanate, ethylene diisocyanate and phthalic acid-bis-isocyanato-ethylester.

Further diisocyanates are, e.g., trimethylhexamethylene diisocyanate, 1,4-diisocyanatobutane, 1,12-diisocyanatododecane and dimer fatty acid diisocyanate.

Instead of or in addition to any of the above diisocyanates, the respective diisothiocyanates can be employed.

In particular hexamethylene diisocyanate and 1-isocyanato-4-(4-isocyanatobenzyl)benzene are suitable, which are shown as representatives of aliphatic and aromatic diisocyanates in following Table A ($R^1$, $R^2$ and $R^3$ being $OCH_3$; $R^4$ being —$CH_2$—O—$(CH_2)_3$—, the propylene residue being bound to the Si atom and the methylene group being bound to the cyclic dithiocarbonate group; and $R^5$ being hydrogen).

TABLE A

| entry | diamine | X | B | time (h) | yield (%) | $M_n^a$ | $M_w^a$ | $PDI^a$ |
|---|---|---|---|---|---|---|---|---|
| 1 | | | ⟨phenylene⟩ | 40 | 85 | 12800 | 19800 | 1.55 |

TABLE A-continued

| entry | diamine | X | B | time (h) | yield (%) | $M_n^a$ | $M_w^a$ | $PDI^a$ |
|---|---|---|---|---|---|---|---|---|
| 2 | | | (bis-methylphenyl-methane) | 40 | 90 | 19300 | 38100 | 1.97 |
| 3 | piperazine (HN-NH) | O | $-(CH_2)_6-$ | 40 | 71 | 20700 | 77900 | 3.76 |
| 4 | | | (1,3-diethyl-cyclohexyl) | 40 | 87 | 18400 | 37500 | 2.04 |
| 5 | | S | (p-phenylene) | 40 | 65 | 3730 | 6160 | 1.65 |
| 6 | | | (p-phenylene) | 40 | 71 | 3180 | 5120 | 1.61 |
| 7 | | | (bis-methylphenyl-methane) | 40 | 58 | 4550 | 7410 | 1.63 |
| 8 | MeHN-CH2CH2-NHMe | O | $-(CH_2)_6-$ | 40 | 71 | 4120 | 7700 | 1.87 |
| 9 | | | (1,3-diethyl-cyclohexyl) | 40 | 66 | 3720 | 5990 | 1.61 |
| 10 | | S | (p-phenylene) | 40 | 70 | 1670 | 2620 | 1.57 |

$^a$Estimated by size exclusion chromatography (eluent: THF; polystyrene standard).

The polymers obtained by the above described reaction with diamines and isocyanates can be effectively crosslinked by condensation reaction of the alkoxysilyl groups $R^1$, $R^2$ and/or $R^3$, upon being exposed to moisture, giving a solvent-resistant, durable material.

Apart from the polymerization of the siloxy group by sol-gel formation a polymerization of cycDTC-Si induced by cationic initiators such as trifluoromethane sulfonic acid alkyl esters, alkyl triflates, Lewis acids or tin tetrachloride, or photo latent initiators such as diaryliodonium salt, can be performed to give the corresponding polymer having siloxy moieties in the side chain, which are also compounds of the present invention (Scheme 11).

Scheme 11

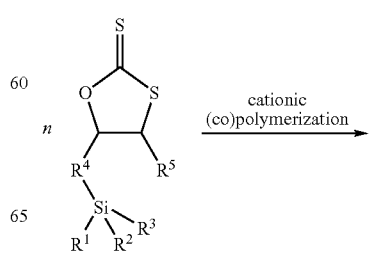

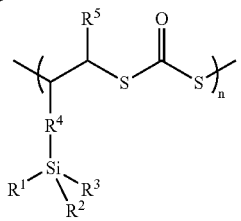

$n = 2$ to $1000$

The main chain consists of a poly(dithiocarbonate), which has a high reflective index. The polymer can be cured by sol-gel reaction of the siloxy moiety in the side chain. The obtained cured material or cured coating layers can be used as optical materials. In the above reaction it is possible to substitute any conventional cycDTC for a part of cycDTC-Si. The term conventional cycDTC comprises any commercially available cycDTC, such as, e.g., cycDTC-OPh (i.e., 5-(phenoxymethyl)-1,3-oxathiolane-2-thione).

In addition, based on the possible irradiation caused depolymerization of poly(dithiocarbonate), micropatterns can be fabricated on material surfaces using masks that only partially cover the coated substrate surface (Scheme 12). Such micropatterns can be employed in photo-electronics devices such as photo-circuits.

chased from Shin-etsu Chemical Co., Ltd. Other reagents were purchased from Wako Chemical Co., Ltd. Solution NMR spectra (400 MHz $^1$H, $\delta_{CHCl3}$=7.26 ppm; 100.6 MHz $^{13}$C, $\delta_{CHCl3}$=77.00 ppm; 79.5 MHz $^{29}$Si, $\delta_{TMS}$=0.00 ppm) were obtained on a Varian NMR spectrometer model Unity INOVA. Solid-state NMR spectra (100.6 MHz $^{13}$C, $\delta_{TMS}$=0.00 ppm; 79.5 MHz $^{29}$Si, $\delta_{TMS}$=0.00 ppm) were obtained on a Bruker NMR spectrometer model DSX400 by use of HPDEC (dipole decoupling) method. IR spectra were obtained on a JASCO FT/IR-460 plus. Number average molecular weight ($M_n$) and weight average molecular weight ($M_w$) were estimated from size exclusion chromatography (SEC), performed on a Tosoh chromatograph model HLC-8120GPC equipped with Tosbh TSK gel-SuperHM-H styrogel columns molecular weight analysis (6.0 mm $\phi \times 15$ cm), using tetrahydrofuran as an eluent at the flow rate of 0.6 mL/min after calibration with polystyrene standards. SEM-image and elemental analysis data were obtained using SEM/EDX (Hitachi SEM/EDX III typeN, Horiba EX-7000) at an accelerating voltage of 25 kV, and the sample was not sputter-coated.

Preparation of cycDTC-Si of the Invention

The synthetic route for the preparation of different cycDTC-Si is shown in Schemes 13 and 14.

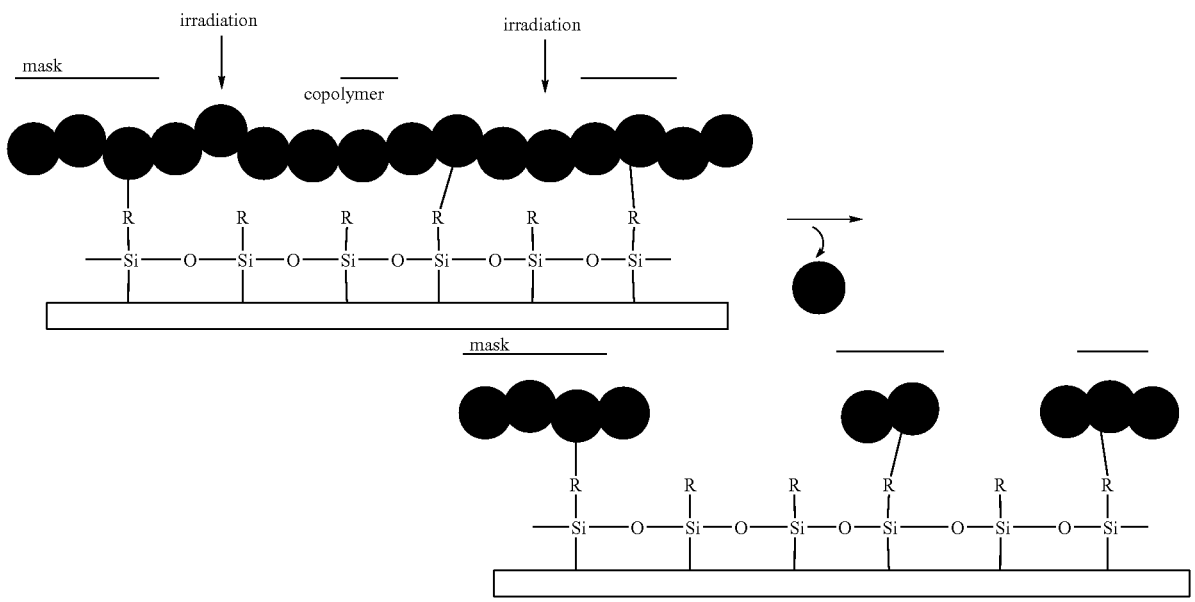

Scheme 12

Any of the compounds or sol-gels of the invention described for use in adhesive formulations and sealant compositions are preferably used in a concentration of up to 20 wt.-%, more preferably 0.1 to 10 wt.-% and most preferably 1 to 5 wt.-%, based on the total weight of the adhesive or sealant composition.

PREPARATION EXAMPLES

If not otherwise specified, all reagents and solvents were used as purchased. Silanes having a epoxy moiety were pur- To a solution of (3-glycidoxypropyl)trimethoxy-silane (X=methoxy; 75.6 g, 320 mmol) and lithium bromide (1.38 g, 16.0 mmol) in tetrahydrofuran (250 ml), a solution of carbon disulfide (29.2 g, 384 mmol) in tetrahydrofuran (150 ml) was added dropwise at 0° C., and the mixture was stirred at 25° C. After 12 h, the volatiles were removed under reduced pressure, and the residue was dissolved in diethylether (500 ml), washed with saturated distilled water (200 ml) three times. The ether layer was dried over magnesium sulfate, filtered, and concentrated under reduced pressure. The residue was distilled under vacuum to give 5-(3-trimethoxysilylpropyloxymethyl)-1,3-oxathiolane-2-thione (1a) as a yellow oil (51.2 g, 164 mmol, 51%).

$Bp_{0.34}$=164° C.; $^1$H-NMR (CDCl$_3$, 20° C.) 5.23 (m, 1H, —CH$_2$—CH(—O—)—CH$_2$—), 3.80 and 3.73 (two dd, 2H, —S—CH$_2$—CH(—O—)—), 3.69 and 3.60 (two dd, 2H, —CH(—O—)—CH$_2$—O—), 3.58 (s, 9H, —Si—(OCH$_3$)$_3$), 3.53 (t, 2H, —O—CH$_2$—CH$_2$—), 1.68 (m, 2H, —CH$_2$—CH$_2$—CH$_2$—), 0.67 (m, 2H, —CH$_2$—CH$_2$—Si—) ppm; $^{13}$C-NMR (CDCl$_3$, 20° C.) 211.9 (—S—C(=S)—O—), 89.2 (—CH$_2$—CH(—O—)—CH$_2$—), 73.8 (—O—CH$_2$—CH$_2$—), 69.1 (—CH(—O—)—CH$_2$—O—), 50.4 (—Si—(O—CH$_3$)$_3$), 36.0 (—S—CH$_2$—CH(—O—)—), 22.6 (—CH$_2$—CH$_2$—CH$_2$—), 5.0 (—CH$_2$—CH$_2$—Si—) ppm; $^{29}$Si-NMR (CDCl$_3$, 20° C.) –42.0 ppm; IR (neat) 2941, 2840, 1456, 1440, 1346, 1231, 1192, 1080, 821 cm$^{-1}$.

By a similar procedure, from (3-glycidoxypropyl)dimethoxymethylsilane (X=Me) (10.0 g, 45.5 mmol), 5-[3-(dimethoxymethysilyl)propyloxymethyl]-1,3-oxathiolane-2-thione (1b) was obtained (11.0 g, 37.2 mmol, 82%).

$Bp_{0.22}$=155° C.; $^1$H-NMR (CDCl$_3$, 20° C.) 5.23 (m, 1H, —CH$_2$—CH(—O—)—CH$_2$—), 3.81 and 3.75 (two dd, 2H, —S—CH$_2$—CH(—O—)—), 3.70 and 3.61 (two dd, 2H, —CH(—O—)—CH$_2$—O—), 3.52 (s, 6H, —Si—(OCH$_3$)$_2$), 3.51 (t, 2H, —O—CH$_2$—CH$_2$—), 1.66 (m, 2H, —CH$_2$—CH$_2$—CH$_2$—), 0.65 (m, 2H, —CH$_2$—CH$_2$—Si—), 0.13 (s, 3H, —Si—CH$_3$) ppm; $^{13}$C-NMR (CDCl$_3$, 20° C.) 211.8 (—S—C(=S)—O—), 89.2 (—CH$_2$—CH(—O—)—CH$_2$—), 73.8 (—O—CH$_2$—CH$_2$—), 69.0 (—CH(—O—)—CH$_2$—O—), 49.9 (—Si—O—(CH$_3$)$_2$), 35.8 (—S—CH$_2$—CH(—O—)—), 22.5 (—CH$_2$—CH$_2$—CH$_2$—), 8.8 (—CH$_2$—CH$_2$—Si—), –6.1 (—Si—CH$_3$) ppm; $^{29}$Si-NMR (CDCl$_3$, 20° C.) –1.4 ppm; IR (neat) 2937, 2870, 2834, 1455, 1440, 1346, 1259, 1231, 1192, 1085, 838, 802, 769 cm$^{-1}$.

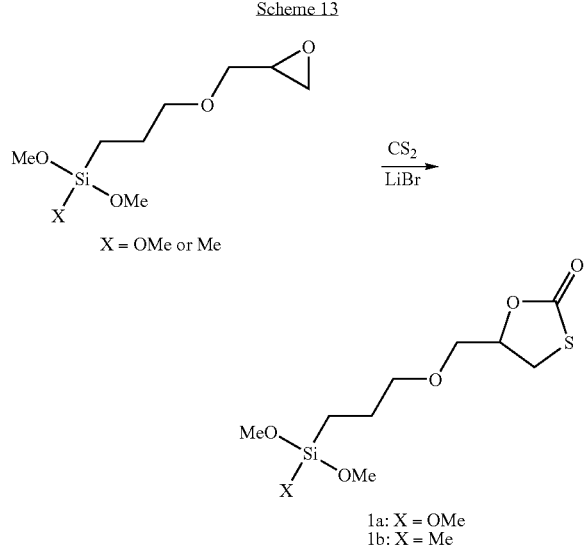

Scheme 13

X = OMe or Me

1a: X = OMe
1b: X = Me

The dithiocarbonate 1c (obtained as a mixture with the corresponding isomer 1c') can be synthesized similarly, as shown in Scheme 14.

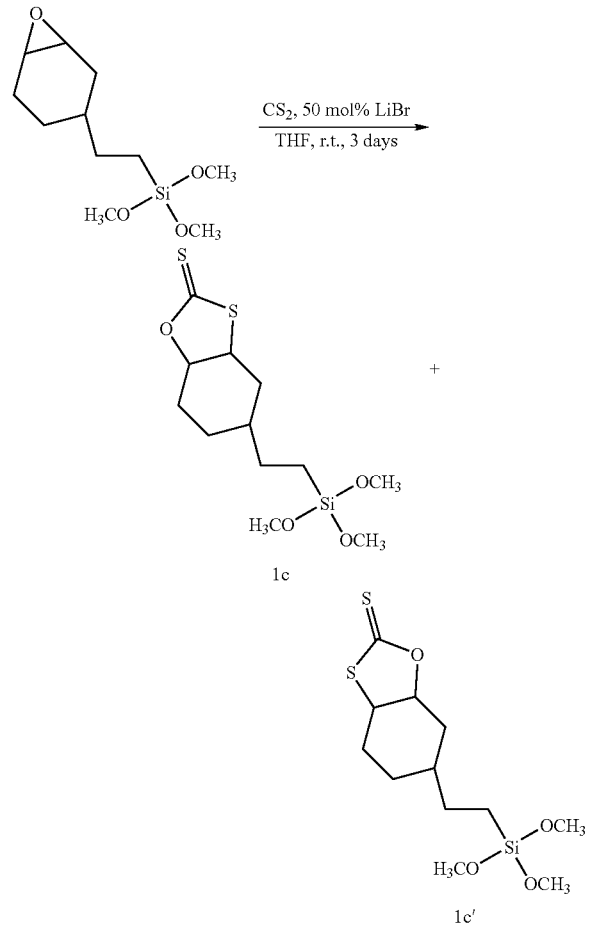

Scheme 14

1c

1c'

A solution of carbon disulfide (1.97 g, 29.3 mmol) in tetrahydrofuran (20 ml) was added dropwise to a mixture of 2-(3,4-epoxycyclohexyl)ethyltriethoxysilane (EETS) (5.12 g, 20.8 mmol) and lithium bromide (0.907 g, 10.4 mmol) in tetrahydrofuran (40 ml) at room temperature for 1 hour. The resulting mixture was stirred at room temperature for 3 days. After the volatiles were removed under reduced pressure, the residue was dissolved in diethylether (50 ml). The solution was washed with saturated NaCl$_{(aq)}$ (100 ml) and distilled water (100 ml), and the obtained organic layer was dried over magnesium sulfate over night. The solution was filtrated and concentrated under reduced pressure, and the residue was dissolved in chloroform (15 ml), and was fractionated by preparative GPC to give a mixture of 2-{3,4-(1,3-oxathiolane-2-thionyl)cyclohexyl}-ethyltriethoxysilane (1c) and 2-{4,5-(1,3-oxathiolane-2-thionyl)cyclohexyl}-ethyltriethoxysilane (1c') as a yellow oil (1.37 g, 4.36 mmol, 21%).

The ratio 1c:1c' was found to be 1:1 by $^1$H-NMR analysis of the mixture: $^1$H-NMR (CDCl$_3$, 20° C.) 4.48 (two t), 4.35-4.22 (m), 4.05 (two t), 3.88 (two t), 3.74-3.52 (m), 3.30-3.11 (m), 2.41-0.82 (m), 0.69-0.61 (m) ppm; $^{13}$C-NMR (CDCl$_3$, 20° C.) 212.4 and 212.2 (—S—C(=S)—O—), 126.9 and 126.4 (—CH(—S—)—CH(—O—)—CH$_2$—), 53.1, 52.6, 51.8, 51.7, 50.5 and 50.4 (—Si—O—(CH$_3$)$_3$), 36.7, 36.0, 35.7, 35.1, 32.9, 32.6, 32.1, 31.3, 31.2, 30.2, 29.3, 28.8, 28.7, 26.5, 25.2, 25.2, 23.9, 23.4, 6.1 and 6.0 (—CH$_2$—CH$_2$—Si—) ppm; $^{29}$Si-NMR (CDCl$_3$, 20° C.) –41.0, –41.4, −41.4, −42.6 ppm; IR (neat) 2938, 2839, 2871, 1746, 1455, 1411, 1339, 1276, 1248, 1196, 1085, 1005, 973, 885, 804, 657 cm$^{-1}$.

Ring Opening of cycDTC-Si with Amines 1 reacts with amines to modify them into the corresponding thiols (Scheme 15). The siloxy group was not affected by the reaction.

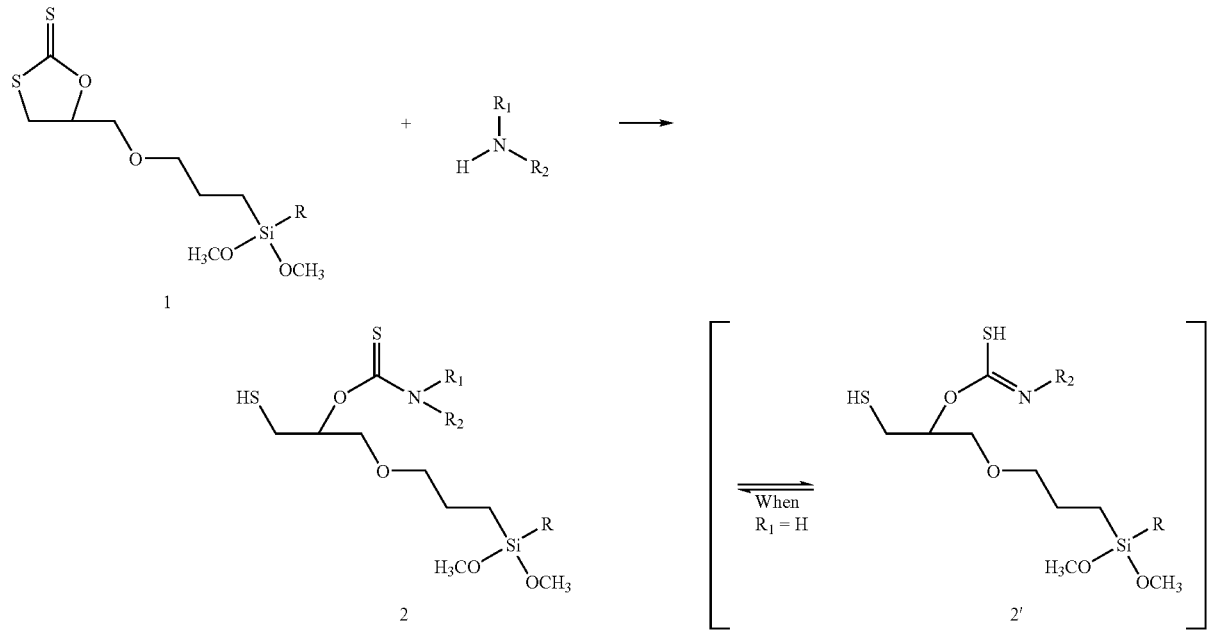

Scheme 15

Reaction of 1 with Diethylamine

Diethylamine (1.05 g, 14.3 mmol) was added to 1a (0.855 g, 2.74 mmol) at room temperature, and the resulting mixture was stirred at room temperature for 10 minutes. Excess diethylamine was removed under reduced pressure to give 2a (R=methoxy, $R_1=R_2$=ethyl; 0.898 g, 2.33 mmol, 85%) as an yellow oil.

$^1$H-NMR (CDCl$_3$, 20° C.): 5.63 (m, 1H, —CH$_2$—CH(—O—)—CH$_2$—), 3.82 (q, 2H, —N—CH$_2$—CH$_3$), 3.78 and 3.68 (two dd, 2H, —CH(—O—)—CH$_2$—O—), 3.57 (s, 9H, —Si—(OCH$_3$)$_3$), 3.50-3.43 (m, 4H, —N—CH$_2$—CH$_3$ and —O—CH$_2$—CH$_2$—), 2.92 (m, 2H, —CH(—O—)—CH$_2$—SH), 1.71-1.62 (m, 2H, —CH$_2$—CH$_2$—CH$_2$—), 1.44 (t, 1H, —CH$_2$—SH), 1.25 (t, 3H, —N—CH$_2$—CH$_3$), 1.18 (t, 3H, —N—CH$_2$—CH$_3$), 0.69-0.66 (m, 2H, —CH$_2$—CH$_2$—Si—) ppm; $^{13}$C-NMR (CDCl$_3$, 20° C.) 186.0 (—O—C(=S)—N—), 79.0 (—CH$_2$—CH(—O—)—CH$_2$—), 73.2 (—O—CH$_2$—CH$_2$—), 68.9 (—CH(—O—)—CH$_2$—O—), 50.3 (—Si—(OCH$_3$)$_3$), 47.7 and 43.4 (—N—CH$_2$—CH$_3$), 24.7 (—CH(—O—)—CH$_2$—SH), 22.6 (—CH$_2$—CH$_2$—CH$_2$—), 13.1 and 11.7 (—N—CH$_2$—CH$_3$), 5.1 (—CH$_2$—CH$_2$—Si—) ppm; $^{29}$Si-NMR (CDCl$_3$, 20° C.) −41.7 ppm; IR (neat) 2972, 2940, 2871, 2840, 2556(SH), 1506, 1429, 1316, 1283, 1244, 1174, 1087, 821, 792 cm$^{-1}$.

A similar reaction of 1b (0.526 g, 1.77 mmol) with diethylamine (0.667 g, 9.12 mmol) gave 2b (R=methyl, $R_1=R_2$=ethyl; 0.523 g, 1.42 mmol, 80%).

$^1$H-NMR (CDCl$_3$, 20° C.) 5.63 (m, 1H, —CH$_2$—CH(—O—)—CH$_2$—), 3.82 (q, 2H, —N—CH$_2$—CH$_3$), 3.77 and 3.68 (two dd, 2H, —CH(—O—)—CH$_2$—O—), 3.52 (s, 6H, —Si—(OCH$_3$)$_2$), 3.50-3.42 (m, 4H, —N—CH$_2$CH$_3$ and —O—CH$_2$—CH$_2$—), 2.92 (m, 2H, —CH(—O—)—CH$_2$—SH), 1.67-1.59 (m, 2H, —CH$_2$—CH$_2$—CH$_2$—), 1.44 (t, 1H, —CH$_2$—SH), 1.25 (t, 3H, —N—CH$_2$—CH$_3$), 1.19 (t, 3H, —N—CH$_2$—CH$_3$), 0.65-0.61 (m, 2H, —CH$_2$—CH$_2$—Si—), 0.12 (s, 3H, —Si—CH$_3$); $^{13}$C-NMR (CDCl$_3$, 20° C.) 186.0 (—O—C(=S)—N—), 79.0 (—CH$_2$—CH(—O—)—CH$_2$—), 73.5 (—O—CH$_2$—CH$_2$—), 68.9 (—CH(—O—)—CH$_2$—O—), 50.0 (—Si—(OCH$_3$)$_2$), 47.7 and 43.3 (—N—CH$_2$—CH$_3$), 24.7 (—CH(—O—)—CH$_2$—SH), 22.7 (—CH$_2$—CH$_2$—CH$_2$—), 13.1 and 11.7 (—N—CH$_2$—CH$_3$), 8.9 (—CH$_2$—CH$_2$—Si), −6.0 (—Si—CH$_3$) ppm; $^{29}$Si-NMR (CDCl$_3$, 20° C.) −1.24 ppm; IR (neat) 2972, 2936, 2871, 2834, 2551(SH), 1508, 1429, 1350, 1317, 1283, 1244, 1173, 1086, 837, 801, 769 cm$^{-1}$.

Reaction of 1a with Benzylamine

Benzylamine (0.205 g, 1.91 mmol) was added to 1a (0.626 g, 2.00 mmol) at room temperature, and the resulting mixture was stirred at room temperature for 10 minutes. The resulting product was dissolved in tetrahydrofuran (10 ml), and poured into hexane (200 ml) to obtain a mixture of the corresponding adduct 2c (R=methoxy, $R_1$=H, $R_2$=CH$_2$Phenyl) and the corresponding tautomer 2c' (R=methoxy, $R_2$=CH$_2$Phenyl) as an oil (0.711 g, 86%).

IR (neat) 3268 (NH), 3030, 2941, 2840, 2568 (SH), 1742, 1658, 1524, 1455, 1401, 1344, 1247, 1182, 1079, 820, 699 cm$^{-1}$; $^{29}$Si-NMR (CDCl$_3$, 20° C.) −41.7, −41.8 ppm; 2c: $^1$H-NMR (CDCl$_3$, 20° C.): 7.38-7.25 (m, C$_6$H$_5$), 6.72 (m, —C (=S)—NH—CH$_2$— of adduct), 5.60-5.57 (m, —CH$_2$—CH(—O—)—CH$_2$—), 4.76-4.73 (m, —NH—CH$_2$-Ph), 3.82-3.62 (m), 3.56 (s, —Si—(OCH$_3$)$_3$ of adduct), 3.49-3.42 (m), 2.91-2.88 (m, —CH (—O—)—CH$_2$—SH), 1.72-1.60 (m, —CH$_2$—CH$_2$—CH$_2$—), 1.49 (t, —CH$_2$—SH of adduct), 0.69-0.64 (m, —CH$_2$—CH$_2$—Si—) ppm; $^{13}$C-NMR (CDCl$_3$, 20° C.) 189.3 (—O—C(=S)—N— of adduct), 136.4 (ipso-Ph of adduct), 128.3 (m-Ph of tautomer), 128.3 (m-Ph of adduct), 127.4, 127.3, 127.3, 127.2 (o-Ph and p-Ph, 80.1 (tautomer), 78.7 (adduct), 74.8, 73.4, 73.4, 72.7, 68.7, 68.6, 48.8, 31.9, 24.3, 23.4, 22.4, 22.3, 4.81, 4.79 ppm.

2c': This tautomer was distinguished from 2c by the following signals in $^1$H-NMR spectrum of the mixture: $^1$H-NMR (CDCl$_3$, 20° C.) 6.94 (m, —N=C—SH of tautomer), 3.57 (s, —Si—(OCH$_3$)$_3$ of tautomer), 1.34 (t, —CH$_2$—SH of tautomer), $^{13}$C-NMR (CDCl$_3$, 20° C.): 188.3 (—O—C(—SH)=N— of tautomer), 136.6 (ipso-Ph of tautomer).

Reaction of 1a with Dibenzylamine

Dibenzylamine (2.28 g, 11.6 mmol) was added to 1a (0.750 g, 2.00 mmol) at room temperature, and the resulting mixture was stirred at room temperature for 15 hours. The conversion was estimated at 52% by $^1$H-NMR analysis. By $^1$H-NMR analysis of the mixture, formation of the corresponding adduct 2d (R=methoxy, R$_1$=R$_2$=CH$_2$Phenyl) was confirmed.

$^1$H-NMR (CDCl$_3$, 20° C.): 7.39-7.17 (m, C$_6$H$_5$), 5.74-5.72 (m, —CH$_2$—CH(—O—)—CH$_2$—), 5.13 (s, —N—CH$_2$-Ph), 4.68-4.57 (dd, —N—CH$_2$-Ph), 3.82-3.56 (m), 3.55 (s, —Si—(OCH$_3$)$_3$), 3.54-3.39 (m), 2.92-2.86 (m, —CH(—O—)—CH$_2$—SH), 1.74-1.64 (m, —CH$_2$—CH$_2$CH$_2$—), 1.34 (t, —CH$_2$—SH), 0.69-0.62 (m, —CH$_2$—CH$_2$—Si—) ppm.

Reaction of 1a with Piperazine

A solution of piperazine (116 mg, 1.35 mmol) in THF (2 mL) was added to 1a (828 mg, 2.65 mmol) at room temperature. After the resulting mixture was stirred at room temperature for 20 hours, volatile fractions were removed under reduced pressure to obtain crude 2e, which was subsequently reacted with 1,4-phenylene diisocyanate as shown below (Reaction of the Thiol Group with Diisocyanate).

Reactions of the Thiol Moiety after Cleavage of cycDTC-Si

Reaction of the Thiol Group with Epoxide

A mixture of glycidyl phenyl ether (0.650 g, 4.33 mmol) and 2a, prepared from 1a (1.25 g, 4.01 mmol) and diethylamine (1.44 g 19.6 mmol), was stirred at room temperature for 6 days (Scheme 16). Complete consumption of 2a was confirmed by $^1$H-NMR analysis. The resulting product was dissolved in tetrahydrofuran (20 ml), and poured into hexane (200 ml) to obtain the crude product as an oil, which was fractionated by preparative GPC to obtain 3-(3-phenoxy-2-hydroxypropyloxy)-2-(N,N-diethylthioureoxy)-1-(3-trimethoxy-silylpropyloxy)propane (3) (0.345 g, 0.644 mmol, 16%).

$^1$H-NMR (CDCl$_3$, 20° C.), 7.28 (t, 2H, Ph(m-H)), 6.96 (t, 1H, Ph(p-H), 6.92 (d, 2H, Ph(o-H), 5.75-5.68 (m, 1H, —CH$_2$—CH(—O—)—CH$_2$—), 4.20-4.13 (m, 1H, —CH$_2$—CH(OH)—CH$_2$—), 4.08-3.66 (m, 6H, —N—CH$_2$—CH$_3$, —CH(—O—)—CH$_2$—O—, —CH(—OH)—CH$_2$—O—), 3.56 (s, 9H, —Si—(OCH$_3$)$_3$), 3.52-3.38 (m, 4H, —N—CH$_2$—CH$_3$ and —O—CH$_2$—CH$_2$—), 3.06-2.76 (m, 4H, —CH(—O—)—CH$_2$—S— and —CH(—OH)—CH$_2$—S—), 1.71-1.63 (m, 2H, —CH$_2$—CH$_2$—CH$_2$—), 1.24 (t, 3H, —N—CH$_2$—CH$_3$), 1.17 (t, 3H, —N—CH$_2$—CH$_3$), 0.68-0.64 (m, 2H, —CH$_2$—CH$_2$—Si—) ppm; $^{13}$C-NMR (CDCl$_3$, 20° C.) 186.1 (—O—C(=S)—N—), 158.4 (Ph (ipso-C), 129.4 (Ph(m-C), 121.0 (Ph(p-C), 114.5 (Ph(o-C), 77.9 and 77.8 (—CH$_2$—CH(—O—)—CH$_2$—) 73.3 (—O—CH$_2$—CH$_2$—), 70.3 and 70.2 (—CH(—O—)—CH$_2$—O—), 69.7 and 69.6(—CH(—OH)—CH$_2$—O—), 68.8 and 67.9 (—CH$_2$—CH(—OH)—CH$_2$—), 50.4 (—Si—(OCH$_3$ )$_3$), 47.8 and 43.4(—N—CH$_2$—CH$_3$), 36.1 and 36.0 (—CH(—O—)—CH$_2$—S—), 22.7 (—CH$_2$—CH$_2$—CH$_2$—), 13.2 and 11.8 (—N—CH$_2$—CH$_3$), 5.1 (—CH$_2$—CH$_2$—Si—) ppm; $^{29}$Si-NMR (CDCl$_3$, 20° C.) –41.7 ppm; IR (neat) 3409 (OH), 3060, 2966, 2940, 2872, 2839, 1651, 1599, 1587, 1506, 1457, 1430, 1379, 1362, 1350, 1316, 1284, 1245, 1173, 1084, 917, 819, 792, 756, 692 cm$^{-1}$.

Scheme 16

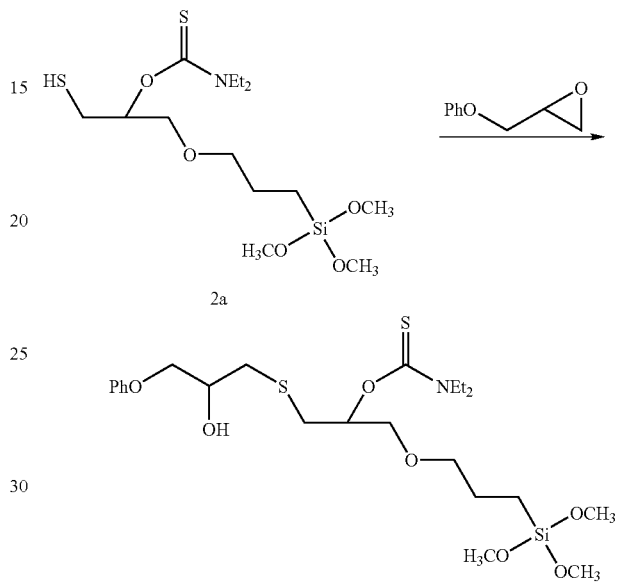

Reaction of the Thiol Group with Isocyanate

Scheme 17

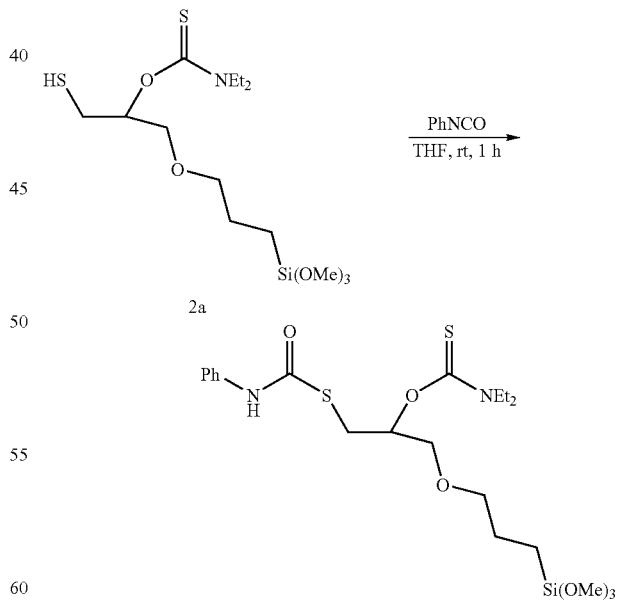

A mixture of phenyl isocyanate (142 mg, 1.19 mmol) and 2a, prepared from 1a (321 mg, 1.03 mmol and diethylamine (358 mg, 4.89 mmol), was stirred at room temperature for 1 hour to obtain the corresponding adduct quantitatively: $^1$H-NMR (400 MHz, CDCl$_3$): δ=7.43-7.08 (m, Ph and —C(=O)—NH-Ph, 6H), 5.83-5.77 (m, —CH$_2$—C H(—O—)—CH$_2$—, 1H), 3.81 (q, —N—CH$_2$—CH$_3$, 2H), 3.76-3.66 (dd, —CH(—O—)—CH$_2$—O—, 2H), 3.57 (s, Si—OCH$_3$, 9H), 3.52-3.38 (m, 6H), 1.71-1.65 (m, —CH$_2$—CH$_2$—CH$_2$—, 2H), 1.23 and 1.15 (t, 6H, —CH$_2$—CH$_3$), 0.69-0.65 (m, —CH$_2$—CH$_2$—Si—, 2H).

Reaction of the Thiol Group with Diisocyanate

A solution of 1,4-phenylene diisocyanate (222 mg, 1.39 mmol) in THF (4 ml) was added to crude 2e (see above) at room temperature. Then triethylamine (14.4 mg, 0.142 mmol) was added to the mixture. The resulting mixture was stirred at room temperature for 40 hours. The solution was poured into hexane (300 ml) to obtain a polymer as a precipitate, which was further purified by reprecipitation into hexane (300 ml). As a result, the polymer (993 mg) was isolated as a viscous oil in 85% yield. IR (neat) 3516, 3447, 3273, 2942, 2838, 1686, 1655, 1607, 1556, 1515, 1487, 1437, 1297, 1229, 1155, 1081, 821, 776 cm$^{-1}$; $^1$H-NMR (in CDCl$_3$, at 20° C.) 7.32 (br), 5.75 (br), 4.24-3.65 (br), 3.58 (br, —Si—(OCH$_3$)$_3$), 3.43 (br), 1.65 (br, —CH$_2$—CH$_2$—CH$_2$—), 0.65 (br, —CH$_2$—CH$_2$—Si—); $^{13}$C-NMR (in CDCl$_3$, at 20° C.) 186.7 (—O—C(=S)—N—), 195.0 (—S—C(=O)—N—), 134.3 (Ph), 120.5 (Ph), 78.3, 73.5, 70.1, 50.5, 48.3, 44.2, 30.7, 22.6 (—CH$_2$—CH$_2$—CH$_2$—), 5.2 (—CH$_2$—CH$_2$—Si—); $^{29}$Si-NMR (in CDCl$_3$, at 20° C.) –41.8.

Application of the Obtained Polymer

The obtained polymer was cast on a glass surface and was left for 24 h under air at ambient temperature. The resulting coating layer was insoluble in THF, chloroform and DMF.

Oxidative Coupling Reaction Between Two Thiol Groups

The oxidative coupling reaction of the thiol group of 2a gave the corresponding disulfide (Scheme 18): 2a, prepared from 1a (1.89 g, 6.05 mmol) and diethylamine (2.38 g 32.5 mmol) by the above-mentioned method, was stirred at room temperature under oxygen atmosphere for 8 days. The conversion of 2a was estimated to be 68% by $^1$H-NMR analysis. Fractionation of the crude mixture by preparative GPC gave bis{3-(3-trimethoxysilylpropyloxy)-2-(N,N-diethylthioureoxy)-propane}disulfide (4) (0.078 g, 0.100 mmol, 3%).

$^1$H-NMR (CDCl$_3$, 20° C.): 5.85-5.79 (m, 2H, —CH$_2$—CH(—O—)—CH$_2$—), 3.83-3.72 (m, 8H, —N—CH$_2$—CH$_3$ and —CH(—O—)—CH$_2$—O—), 3.57 (s, 18H, —Si—(OCH$_3$)$_3$), 3.50-3.43 (m, 8H, —N—CH$_2$—CH$_3$ and —O—C H$_2$—CH$_2$—), 3.16-3.14 (m, 4H, —CH(—O—)—C H$_2$—S—), 1.69-1.62 (m, 4H, —CH$_2$—CH$_2$—CH$_2$—), 1.23 (two t, 6H, —N—CH$_2$—CH$_3$), 1.17 (two t, 6H, —N—CH$_2$—CH$_3$), 0.67-0.63 (m, 4H, —CH$_2$—CH$_2$—Si—) ppm; $^{13}$C-NMR (CDCl$_3$, 20° C.) 186.1 (—O—C(=S)—N—), 77.4 (—CH$_2$—CH(—O—)—CH$_2$—), 73.4 (—O—CH$_2$—CH$_2$—), 69.9 and 69.8 (—CH(—O—)—CH$_2$—O—), 50.5 (—Si—(OCH$_3$)$_3$), 47.8 and 43.5 (—N—CH$_2$—CH$_3$), 39.6 and 39.5 (—CH(—O—)—CH$_2$—S—), 22.7 (—CH$_2$—CH$_2$—CH$_2$—), 13.3 and 11.9 (—N—CH$_2$—CH$_3$), 5.2 (—CH$_2$—CH$_2$—Si—) ppm; $^{29}$Si—NMR (CDCl$_3$, 20° C.) –41.7 ppm; IR (neat) 2966, 2939, 2872, 2839, 1507, 1429, 1316, 1283, 1245, 1173, 1087, 820, 792 cm$^{-1}$.

Scheme 18

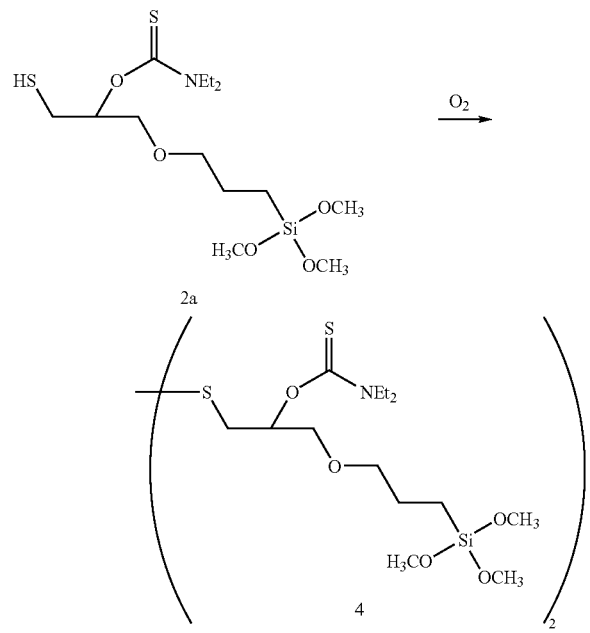

Sol-Gel Formation of the Siloxy Moieties after Ring-Opening of cycDTC-Si

The siloxy moiety of 2 can be applied to sol-gel reaction (Scheme 19): Triethylamine (5.00 mg, 0.049 mmol) and water (37.6 mg, 2.09 mmol) were added to 2a (0.530 g, 1.37 mmol), and the resulting mixture was stirred at room temperature for 1 day. After volatiles were removed under reduced pressure, the residue was washed with tetrahydrofuran (100 ml) to obtain 5a (0.199 g, 38%) as tetrahydrofuran-insoluble parts.

$^{13}$C-NMR (solid-state (HPDEC), 20° C.) 188.5-186.4 (—O—C(=S)—N—), 175.4-165.5, 76.6-68.4, 58.7-30.3, 29.5-20.8, 19.6-5.5 ppm; $^{29}$Si-NMR (solid-state (HPDEC), 20° C.)-65.5--71.8 ppm; IR (KBr) 3445 (OH and NH), 2976, 2933, 2879, 2523 (SH), 1734, 1653, 1559, 1507, 1429, 1362, 1317, 1284, 1245, 1173, 1096, 1063, 1004, 800 cm$^{-1}$.

A similar reaction of 2b gave the corresponding insoluble product 5b.

$^{13}$C-NMR (solid-state (HPDEC), 20° C.) 188.5-170.0 (—O—C(=S)—N— and —O—C(—SH)=N), 138.6-130.0, 124.4-118.3, 108.2-100.5, 77.6-61.6, 51.4-48.7, 48.6-23.3, 22.6-14.1, 9.6--0.7 ppm; $^{29}$Si-NMR (solid-state (HPDEC), 20° C.)-68.6--79.4 ppm; IR (KBr) 3295 (NH), 3033, 2930, 2867, 2606 (SH), 1735, 1653, 1550, 1502, 1455, 1416, 1346, 1269, 1215, 1181, 1104 1029, 738, 721, 695 cm$^{-1}$.

Scheme 19

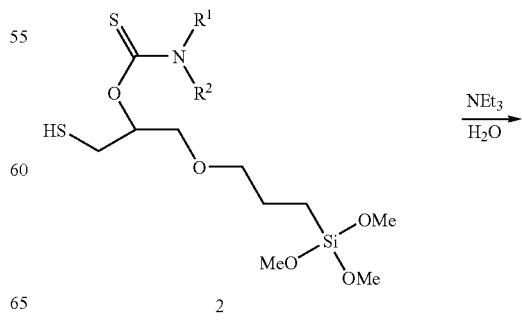

-continued

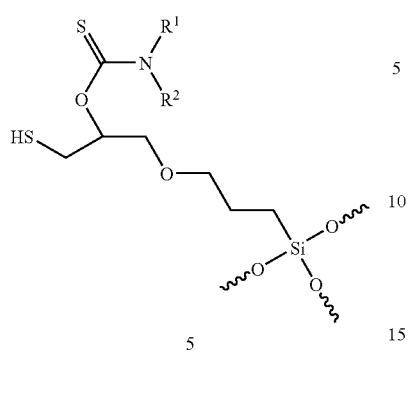

5

Synthesis of Oligosiloxanes, Crosslinked Polysiloxanes and Linear Polysiloxanes Comprising the Cyclic Dithiocarbonate Group Synthesis of Liquid Oligomers Hydrogen chloride diethyl ether complex (HCl/diethylether, 1M in ether, 0.15 ml, 0.15 mmol) was added to mixture of 1a (0.722 g, 2.47 mmol) and distilled water (0.0660 g, 3.67 mmol) at room temperature. After the resulting mixture was stirred at room temperature for 5 hours, volatiles were removed under reduced pressure. The residue was dissolved in THF (30 mL), and poured into hexane (400 mL). Liquid oligomers (Scheme 6) (0.661 g) with $M_n$=320, $M_w$=1620, and PDI=5.1 were isolated as a yellow oil.

The similar reaction of 1a (3.58 g, 11.4 mmol) and distilled water (0.311 g, 17.3 mmol) in the presence of triethylamine (0.0568 g, 0.561 mmol) for 5 h gave the corresponding liquid oligomers (3.28 g, $M_n$=400, $M_w$=1150, and PDI=2.9).

The similar reaction of 1a (0.724 g, 2.32 mmol) and distilled water (0.065 g, 3.61 mmol) in the presence of $CH_3COOH$ (0.0085 g, 0.142 mmol) for 3 days gave the corresponding liquid oligomers (0.699 g, $M_n$=530, $M_w$=640, and PDI=1.2).

Spectral data:

$^1$H-NMR (CDCl$_3$, 20° C.) 5.28 (br, —CH$_2$—CH(—O—)—CH$_2$—), 3.82-3.68 (br), 3.54 (br), 3.48 (s —Si—OCH$_3$), 1.71 (br, —CH$_2$—CH$_2$—CH$_2$—), 0.70 (br, —CH$_2$—CH$_2$—Si—) ppm. $^{13}$C-NMR (CDCl$_3$, 20° C.) 212.3 (br, —S—C(=S)—O—), 89.6 (br, —CH$_2$—CH(—O—)—CH$_2$—), 73.9 (br, —O—CH$_2$—CH$_2$—), 69.5 (br, —CH(—O—)—CH$_2$—O—CH$_2$—), 50.9 (small, —Si—OCH$_3$), 36.0 (—S—CH$_2$—CH(—O—)—), 23.0 (—CH$_2$—CH$_2$—CH$_2$—), 8.6 (—CH$_2$—CH$_2$—Si—) ppm. $^{29}$Si-NMR (CDCl$_3$, 20° C.) −50.3 ((CH$_3$O—)$_2$Si(—O—)(—CH$_2$—)), −59.3 (CH$_3$O—)Si(—O—)$_2$(—CH$_2$—)), −67.9 (—CH$_2$—)Si(—O—)$_3$) ppm. IR (neat): 3427, 2932, 2868, 2810, 1731, 1650, 1439, 1410 1036, 903, 838, 762 cm$^{-1}$.

In the $^1$H-NMR spectrum, a broad signal at 5.28 ppm assigned to —S—CH$_2$—CH(—O—)— in DTC structure was observed. A broad signal at 212.3 ppm assigned to —C(=S)— was confirmed by the $^{13}$C-NMR spectrum. In the $^{29}$Si-NMR spectrum, a signal at −42.0 ppm attributed to 1a had disappeared. Thus, the sol-gel condensation proceeded without damaging the DTC moiety.

Post Curing of Liquid Oligomer

The liquid oligomer (1.0 g), obtained by oligomerization of DTC-silane 1a, was dissolved in THF (10 mL), and was cast on a silicate glass and heated at 80° C. for 24 hours. The resulting layer, immobilized on the glass surface, was insoluble in THF, chloroform, and DMF.

Reaction of the Liquid Oligomer with Amine
Reaction with Butylamine

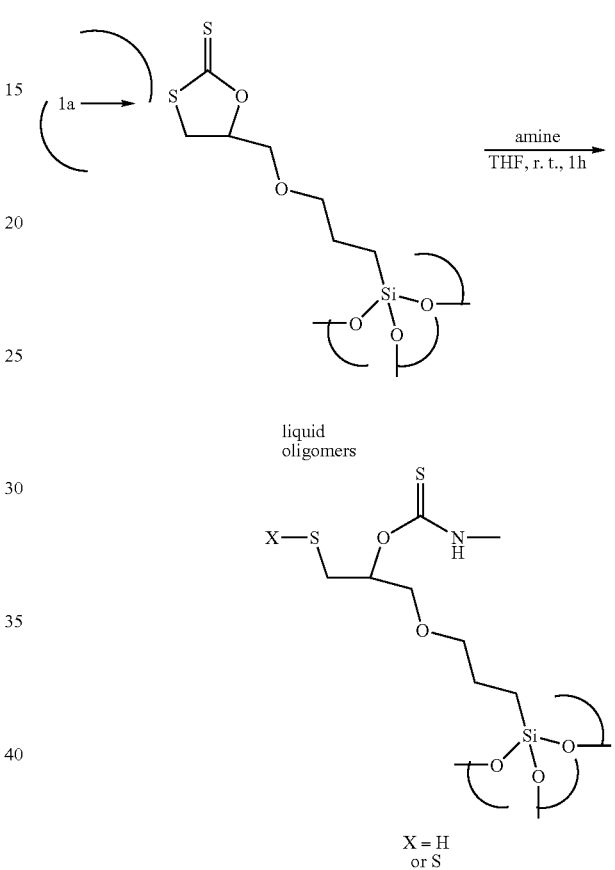

S—S bond can be formed by oxidative coupling of the thiol group, as shown in Scheme 18

To a solution of the liquid oligomer (0.271 g, 0.867 mmol (DTC unit)) (prepared from 1a) in THF (3.5 mL), butylamine (0.0763 g, 1.04 mmol) was added, and the resulting mixture was stirred at room temperature for 1 hour. The resulting insoluble fraction was collected by filtration and washed by THF (30 mL), and was dried under vacuum. The insoluble part (0.207 g, 0.537 mmol (DTC unit)) was obtained in 62% yield.

Reactions with triethylamine, 1,2-diaminoethane and N,N, N-tris(aminomethyl)amine The reactions were carried out in the same manner as shown for the reaction with butylamine except for varying the respective amounts according to the molar ratios shown in the following Table.

TABLE

Reaction of the soluble oligomer with amine.

| entry | amine | $[DTC]_0:[NR^aR^bR^c]_0$ | gel fraction (%) | appearance |
|---|---|---|---|---|
| 1 | $NEt_3$ | 1:1 | 1 was recovered (96%). | — |
| 2 | $\diagup\diagdown\diagup NH_2$ | 2:1 | 66 | yellow gel |
| 3 | | 1:1 | 62 | yellow gel |
| 4 | $H_2N\diagdown\diagup\diagdown NH_2$ | 2:1 | 88 | yellow powder |
| 5 | | 1:1 | 94 | white powder |
| 6 | $H_2N\diagdown N(\diagup NH_2)\diagdown NH_2$ | 3:1 | 97 | yellow powder |
| 7 | | 1:1 | 87 | white powder |

Synthesis of Linear Oligomer and Polymers

Hydrogen chloride diethyl ether complex (HCl/diethylether, 1M in ether, 0.125 ml, 125 mmol) was added to mixture of 1b (0.732 g, 2.47 mmol) and distilled water (0.0681 g, 3.78 mmol) at room temperature. After the resulting mixture was stirred at room temperature for 24 hours, volatiles were removed under reduced pressure. The residue was dissolved in tetrahydrofuran (30 ml), and poured into hexane (400 ml). The mixture of the corresponding linear polymer and oligomer (0.679 g; polymer: $M_n$=5680, $M_w$=9630, PDI=1.7; oligomer: $M_n$=950, $M_w$=1050, PDI=1.1) was obtained as an yellow oil.

The similar reaction of 1b (0.644 g, 2.17 mmol) and distilled water (0.0404 g, 2.24 mmol) in the presence of triethylamine (0.0110 g, 0.109 mmol) gave 0.699 g of the mixture of the corresponding linear polymer ($M_n$=3520, $M_w$=4230, PDI=1.2) and oligomer ($M_n$=820, $M_w$=1060, PDI=1.3).

Spectral Data:

$^1$H-NMR (CDCl$_3$, 20° C.) 5.26 (br, —CH$_2$—CH(—O—)—CH$_2$—), 3.86 -3.59 (br), 3.52-3.48 (br), 1.82-1.66 (br, —CH$_2$—CH$_2$—CH$_2$—), 0.56-0.51 (br, —CH$_2$—CH$_2$—Si—), 0.13-0.10 (br, —Si—CH$_3$) ppm. $^{13}$C-NMR (CDCl$_3$, 20° C.) 212.3-212.0 (—S—C(=S)—O—), 89.9-89.2 (—CH$_2$—CH(—O—)—CH$_2$—), 74.4-74.3 (—O—CH$_2$—CH$_2$—), 69.5-69.2 (—CH(—O—)—CH$_2$—OCH$_2$—), 36.0 (—S—CH$_2$—CH(—O—)—), 23.1-23.0 (—CH$_2$—CH$_2$—CH$_2$—), 13.4-12.9(—CH$_2$—CH$_2$—Si—), -0.26--0.73 (—Si—CH$_3$) ppm. $^{29}$Si-NMR (CDCl$_3$, 20° C.) -19.8, -22.1, -22.8 ppm. IR (neat) 3471, 2932, 2868, 2803, 1731, 1651, 1477, 1439, 1411, 1345, 1258, 1230, 1188, 1044, 914, 801 cm$^{-1}$.

It was confirmed that the polymer and oligomers possessed cycDTC moieties by the analyses of NMR spectra. In the $^{13}$C-NMR spectrum, a signal at around 49 ppm assigned to —O—CH$_3$ was not detected. This indicates that the substitution from —Si—O—CH$_3$ to —Si—OH and the following condensation were completely produced. The products showed three $^{29}$Si-NMR signals at -19.8, -22.1, and -22.8 ppm with the integral ratio of 4:3:2. On the basis of this information, it is expected that the signals of the cyclic trimer, the cyclic tetramer, and the oligomers having more polymerization degree are observed at around -9, -20, and -22 ppm, respectively. Accordingly, a signal at -19.8 ppm was assigned to the cyclic tetramer. Furthermore, in $^{29}$Si-NMR spectrum of the product obtained by the sol-gel reaction in ether, two signals at -19.8 and -22.1 ppm with the integral ratio of 2:1 appeared. In solution reaction, it is expected that the formation of oligomers is prior to the formation of polymers. Signals at -22.1 and -22.8 ppm were reasonably assigned to silicon contained in cyclic or linear oligomers and the chain polymers, respectively.

Synthesis of Crosslinked Polysiloxanes

Hydrogen chloride diethyl ether complex (HCl/diethylether, 1M in ether, 0.15 ml, 0.15 mmol) was added to mixture of 1a (0.763 g, 2.44 mmol) and distilled water (0.0700 g, 3.89 mmol) at room temperature. After the resulting mixture was stirred at room temperature for 24 hours, volatiles were removed under reduced pressure. The residue was washed by CHCl$_3$ (100 ml), to give crosslinked polysiloxane (0.504 g) as an insoluble yellow powder.

The similar reaction of 1a (0.796 g, 2.55 mmol) and distilled water (0.0600 g, 3.33 mmol) in the presence of triethylamine (0.0100 g, 0.102 mmol) gave the corresponding crosslinked polysiloxane (0.539 g).

Spectral Data:

$^{13}$C-NMR (solid-state (HPDEC), 20° C.) 208.6 (—S—C(=S)—O—), 106.6 (—CH$_2$—CH(—O—)—CH$_2$—), 86.4 (—O—CH$_2$—CH$_2$—), 69.2 (—CH(—O—)—CH$_2$—OCH$_2$—), 46.4 (—Si—OCH$_3$), 32.1 (—S—CH$_2$—CH(—O—)—), 19.1 (—CH$_2$—CH$_2$—CH$_2$—), 5.1 (—CH$_2$—CH$_2$—Si—) ppm; $^{29}$Si (solid-state (HPDEC), 20° C.)-57.4--67.6 ppm; IR (neat) 3444 (OH), 2937, 2866, 2804, 1731, 1650, 1441, 1345, 1234, 1193, 1099, 1038 cm$^{-1}$.

A signal at 209 ppm assignable to —C(=S)— was clearly observed in $^{13}$C-NMR spectrum. There is no signal around 180 ppm attributable to ring-opened —C(=S)—. $^{29}$Si-NMR spectrum is very simple, suggesting the higher conversion of the siloxane group into the polysiloxane structure.

Synthesis of Co-Polymerization Products with Trimethoxyvinylsilane

To a mixture of 1a (1.02 g, 3.26 mmol) and trimethoxyvinylsilane, distilled, water (0.168 g, 9.32 mmol) and triethylamine (32.2 mg, 0.318 mmol) were added. By stirring the mixture at room temperature for 18 h, tetrahydrofurane-insoluble crosslinked polysiloxane (0.860 g) and tetrahydrofurane-soluble oligomers (0.228 g) were obtained. In addition Synthesis of Co-Polymerization Products with Glycidoxytrimethoxysilane To a mixture of 1a (0.949 g, 3.04 mmol) and glycidoxytrimethoxysilane (0.723 g, 3.06 mmol), distilled water (0.165 g, 9.15 mmol) and triethylamine (30.1 mg, 0.297 mmol) were added. By stirring the mixture at room temperature for 18 h, tetrahydrofuran-insoluble crosslinked polysiloxane (1.13 g) was obtained.

Modification of Crosslinked Polysiloxane Made of 1a

Diethylamine (0.141 g, 1.93 mmol) was added to the crosslinked polysiloxane made of 1a (0.120 g, 0.384 mmol (amount of cycDTC unit)) at room temperature, and the resulting mixture was stirred at room temperature for 10 minutes. The yellow color of the crosslinked polysiloxane disappeared within 10 minutes, indicating the cycDTC was completely consumed to give a product having acyclic thiourethane and thiol groups. After the volatile fractions were removed under the reduced pressure, the residue was washed by $CHCl_3$ (100 ml), and the insoluble part of the diethylamine modified product (0.128 g, 0.332 mmol (amount of ring-opened DTC unit), 86%) was obtained by filtration.

Spectral Data:
$^{13}C$-NMR (solid-state (HPDEC), 20° C.) 188.5-186.4 (—O—$\underline{C}$(=S)—N—), 175.4-165.5, 76.6-68.4, 58.7-30.3, 29.5-20.8, 19.6-5.5 ppm. $^{29}Si$—NMR (solid-state (HPDEC), 20° C.) -55.2--71.8 ppm. IR (KBr) 3445 (OH), 2976, 2933, 2879, 2523 (SH), 1734, 1653, 1559, 1507, 1429, 1362, 1317, 1284, 1245, 1173, 1096, 1063, 1004, 800 $cm^{-1}$.

In the $^{13}C$-NMR spectrum, while a signal at 209 ppm attributed to —$\underline{C}$(=S)— in DTC moiety had disappeared, broad signals from 189 to 186 ppm assignable to the ring-opened —$\underline{C}$(=S)— were observed. Moreover, ring opening of cycDTC moiety was confirmed by the presence of thiol absorption at 2523 $cm^{-1}$ in the IR spectrum. The $^{29}Si$-NMR spectrum was almost the same as that of the crosslinked polysiloxane made of 1a, indicating that the selective reaction of DTC moiety was achieved without damaging the siloxane backbone.

Cationic Polymerization of cycDTC-Si

To 1a (0.760 g, 2.43 mmol), methyl trifluoromethanesulfonate (24.9 mg, 0.152 mmol) was added at room temperature, and the mixture was stirred at room temperature. After 2 days, complete consumption of cyclic dithiocarbonate unit was confirmed by NMR-analysis. In the $^{13}C$-NMR spectrum, a new signal appeared at 172.5 ppm, attributable to the carbonyl carbon of the acyclic dithiocarbonate, suggesting the formation of the corresponding linear poly(dithiocarbonate). The mixture was dissolved in tetrahydrofuran (5 ml), and the solution was poured into hexane (100 ml) to obtain the corresponding polymer (0.603 g) as precipitates, which were collected by filtration and were dried under vaccum. When the polymer was re-dissolved in tetrahydrofuran, it immediately became insoluble gel by crosslinking, due to moisture-induced sol-gel reaction of the siloxy part in the side chain of the polymer.

Cationic Copolymerization of cycDTC-Si and 5-(Phenoxymethyl)-1,3-oxathiolane-2-thione (i.e. cycDTC-OPh)

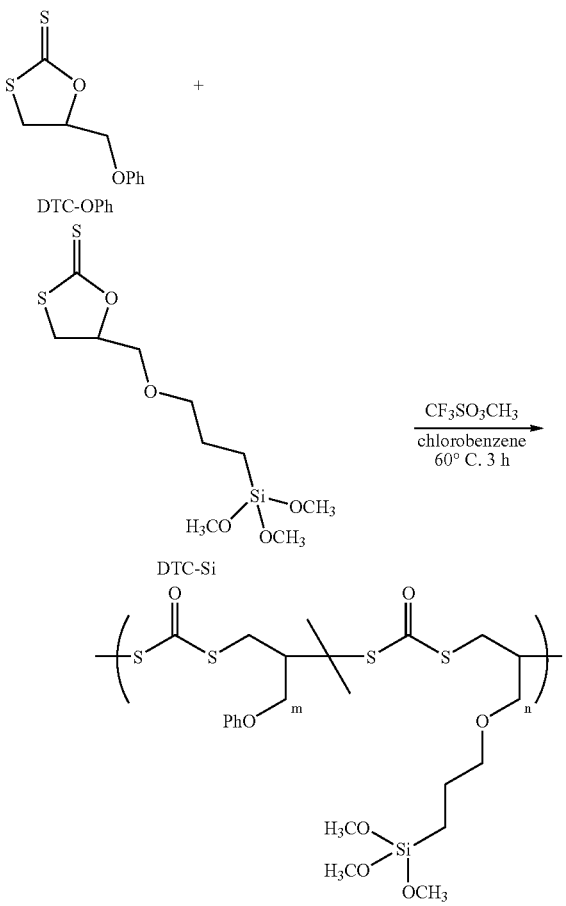

Scheme 21

To a solution of cycDTC-OPh (1088.0 mg, 4.81 mmol) and cycDTC-Si (646.5 mg, 2.07 mmol) (7:3) in chlorobenzene (7 ml), methyl trifluoromethanesulfonate (54.9 mg, 0.335 mmol) was added and the mixture was stirred at 60° C. After 3 hours, triethylamine (2 ml) was added to the mixture to terminate the polymerization. The volatiles were removed under reduced pressure, and the residue was analyzed by $^1H$-NMR to confirm the formation of the corresponding copolymer. By size exclusion chromatography (SEC) of the copolymer, its weight average molecular weight ($M_w$) and polydispersity index (PDI) were estimated as being 3460 g/mol and 2.6, respectively.

APPLICATION EXAMPLES

Coating of Silicate (Glass, Quartz) Surfaces

Coating (Pre-treatment) with cycDTC-Si
A spherical silica-gel particle, SP-120-40/60 (DAISO Co., Ltd.), whose average diameter was 55 μm, was washed with acetone several times to remove organic impurities, then, dried at 100° C. for 3 hour under reduced pressure. To a silica gel (10.30 g) dispersed in anhydrous dimethylformamide (100 ml), 1a (10.30 g, 32.96 mmol) was added and the mixture was stirred at 100° C. After 12 h, the mixture was filtrated through a membrane filter (pore size 0.8 μm), and washed with methanol twice, and further washed with anhydrous tetrahydrofuran in a soxhlet apparatus for 12 hour. The washed silica gel was dried at 60° C. for 5 hours under reduced pressure to obtain 10.33 g of yellowish powder (cycDTC-SiO$_2$).

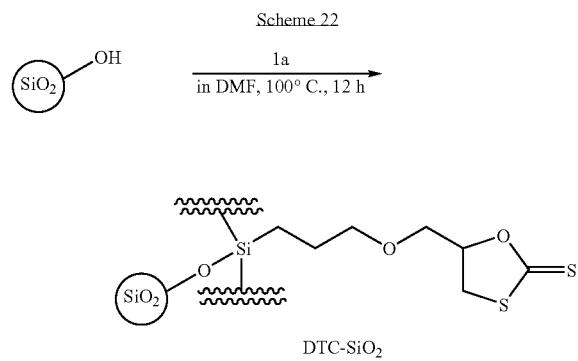

DTC-SiO$_2$

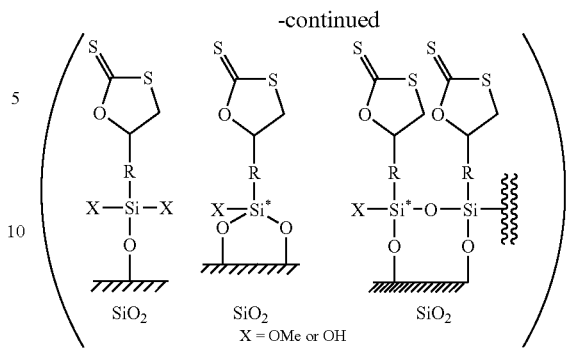

X = OMe or OH

Characterization of the product was performed by SEM, EDX, and elemental analysis.

By the SEM-image of the obtained cycDTC-SiO$_2$, it was confirmed that the spherical shape of the original silica gel particle was maintained. In the EDX spectrum shown below a signal was observed at 2.30 keV to indicate the presence of sulfur atom on the surface of the silica gel particle. Elemental analysis of the modified silica gel revealed that sulfur content was 3.02 wt-% and consequently the immobilization degree of 1a on the silica gel surface was calculated to be 0.472 mmol/g.

Scheme 23
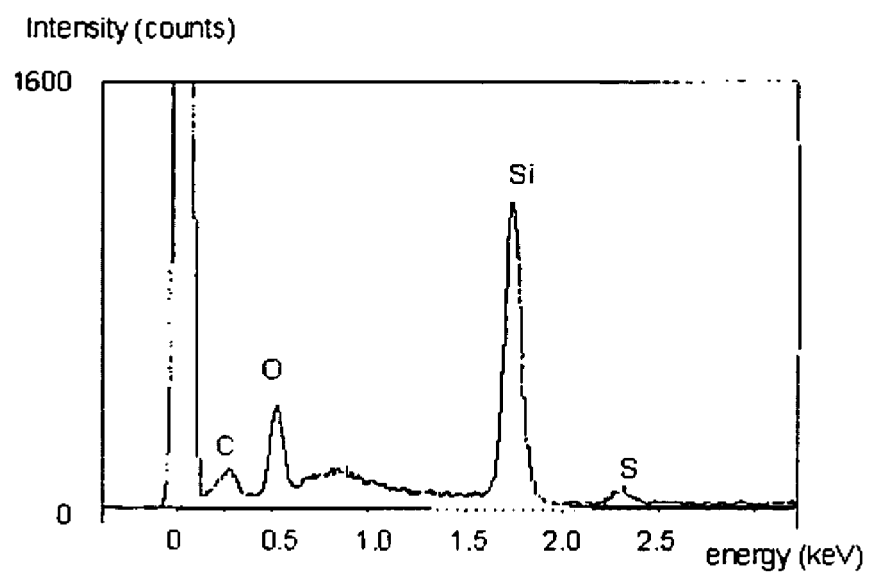
EDX Analysis of cycDTC-SiO$_2$.

Scheme 24 below shows a solid-state $^{29}$Si-NMR spectrum, in which one strong signal due to the silicon atoms of the silica gel was observed around −110 ppm. Two weak signals were also observed around −50 ppm. These weak ones were attributable to the silicon atoms of DTC units bonded to the surface of the silica gel. This NMR analysis suggests that DTC units on the surface of silica gel were covalently bounded by several modes as shown in Scheme 5. The presence of the cycDTC moiety on the silica gel was confirmed by a solid state $^{13}$C-NMR spectrum (Scheme 25), in which there was a signal around 210 ppm attributable to C=S bond: Solid state NMR spectra of cycDTC-SiO$_2$: (a) $^{29}$Si-NMR (Scheme 24). (b) $^{13}$C-NMR Scheme 24
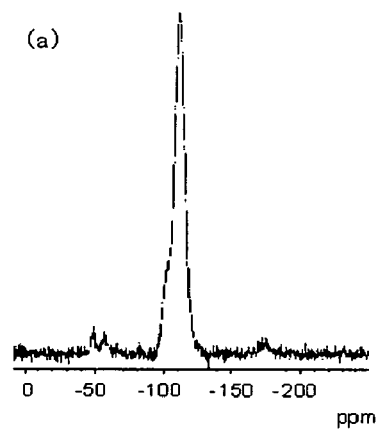
(a)
Scheme 25
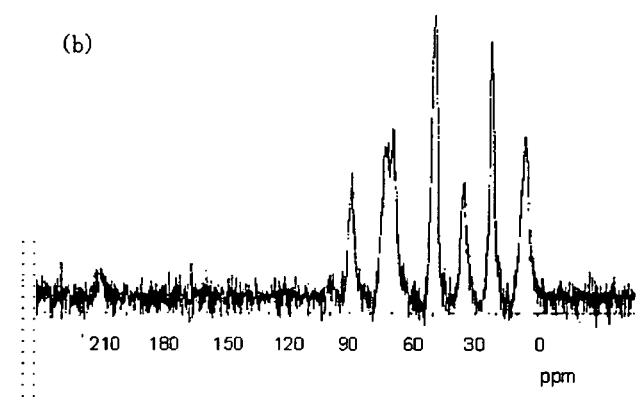
(b)

Coating with Jeffamine® Modified cycDTC-Si

1st Step: Modification of Jeffamine® with 1a into Thiol Having Siloxy Group

Based on the reactivity of 1 with amines, Jeffamine®, a polyether having amino groups at the chain ends was modified into the corresponding polyethers having thiol and siloxy moieties at the chain ends. The procedure is summarized in Scheme 26.

Scheme 26

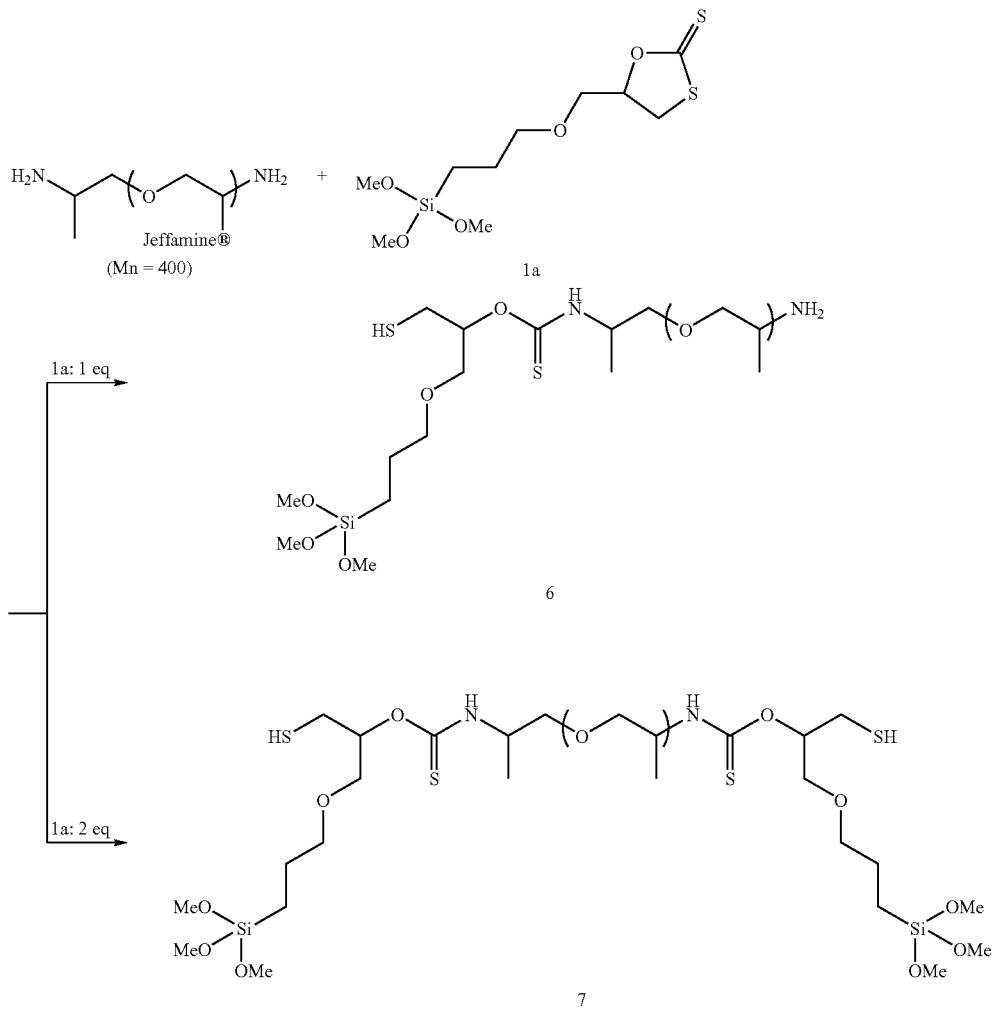

1a (0.950 g, 3.04 mmol) was added to Jeffamine® ($M_n$=400; 1.24 g, 3.09 mmol) at room temperature, and the resulting mixture was stirred at room temperature for 1 day. The obtained oil was dissolved in tetrahydrofuran, and precipitated into hexane to obtain the corresponding modified Jeffamine® 6 (1.66 g, $M_n$=1060, $M_w$=1360, PDI=1.3) as a viscous yellow oil in a yield of 76%. Similarly, reaction of 1a (1.95 g, 6.24 mmol) with Jeffamine® ($M_n$=400; 1.32 g, 3.31 mmol) gave the corresponding modified Jeffamine® 7 (3.04 g, $M_n$=1200, $M_w$=1400, PDI=1.2) as a viscous pale yellow oil in a yield of 93%.

6: $^1$H-NMR(CDCl$_3$, 20° C.): 6.41-5.60 (br, —CH$_2$—C$\underline{H}$(—O—)—CH$_2$—), 4.06-3.91 (br), 3.56 (s, —Si—(OC$\underline{H}_3$)$_3$), 3.51-3.28 (br), 3.17-3.07 (br), —NH$_2$), 2.90-2.83 (br, —CH(—O—)—C$\underline{H}_2$—SH), 1.70-1.64 (m, —CH$_2$—C$\underline{H}_2$—CH$_2$—), 1.20-1.10 (br), 1.01 (d, terminal —O—CH(—C$\underline{H}_3$)—CH$_2$—), 0.69-0.65 (br, —CH$_2$—C$\underline{H}_2$—Si—) ppm; $^{13}$C-NMR (CDCl$_3$, 20° C.) 165.5 (—O—$\underline{C}$(=S)—N—), 76.2-74.8 (br), 73.6-71.6 (br), 67.8, 50.4 (—Si—(O$\underline{C}$H$_3$)$_3$), 46.8, 46.3, 24.7 (—CH(—O—)—$\underline{C}$H$_2$—SH), 22.6 (—CH$_2$—$\underline{C}$H$_2$—CH$_2$—), 19.5 (terminal —O—CH(—$\underline{C}$H$_3$)—CH$_2$—), 18.4-17.0 (internal —O—CH(—$\underline{C}$H$_3$)—CH$_2$—), 5.1 (—CH$_2$—$\underline{C}$H$_2$—Si—) ppm; $^{29}$Si-NMR (CDCl$_3$, 20° C.) −41.7 ppm; IR (neat) 3333 (NH$_2$), 2970, 2940, 2870, 1668, 1549, 1455, 1373, 1344, 1298, 1105, 926, 821 cm$^{-1}$.

7: $^1$H-NMR (CDCl$_3$, 20° C.): 5.58-5.57 (—CH$_2$—C$\underline{H}$(—O—)—CH$_2$—), 4.39 (br), 4.06 (br), 3.78-3.59 (br), 3.57 (s, —Si—(OC$\underline{H}_3$)$_3$), 3.56-3.38 (br), 3.28-3.25 (br), 3.17-3.11 (br), 2.86 (br), 1.72-1.65 (br, —CH$_2$—C$\underline{H}_2$—CH$_2$—), 1.47 (t, —CH$_2$—S$\underline{H}$,), 1.27-1.25 (br, terminal —O—CH(—C$\underline{H}_3$)—CH$_2$—), 1.21-1.10 (br, internal —O—CH(—C$\underline{H}_3$)—CH$_2$—), 0.69-0.63 (br, —CH$_2$—C$\underline{H}_2$—Si—) ppm; $^{13}$C-NMR (CDCl$_3$, 20° C.) 188.2-188.1 (—O—$\underline{C}$(=S)—N—), 79.6, (—CH$_2$—$\underline{C}$H(—O—)—CH$_2$—), 78.3, 75.4-74.8 (br), 73.7-72.7 (br), 72.0-7.08 (br), 68.9-68.8 (—CH(—O—)—$\underline{C}$H$_2$—O), 67.7, 50.3 (—Si—(O$\underline{C}$H$_3$)$_3$), 25.4, 24.5-24.4 (—CH(—O—)—$\underline{C}H_2$ —SH), 22.6-22.5 (—$CH_2$—$\underline{C}H_2$—$CH_2$—), 17.6-16.5 (internal —O—CH(—$\underline{C}H_3$)—$CH_2$—), 5.1-5.0 (—$CH_2$—$\underline{C}H_2$—Si—) ppm; $^{29}$Si-NMR ($CDCl_3$, 20° C.) −41.8 ppm; IR (neat) 3299 (NH), 2969, 2938, 2870, 2841, 2555 (SH), 1677, 1520, 1457, 1374, 1345, 1300, 1258, 1196, 1092, 927, 822 $cm^{-1}$.

2$^{nd}$ Step: Coating of a Glass Surface by Curing Reaction of the Modified Jeffamines®

Based on the reactivities of the thiol and siloxy groups of the adducts of 1 with amines (see Scheme 18 and Scheme 19), the modified Jeffamines® 6 and 7 were applied to coating of a glass surface (Scheme 27): The modified Jeffamine® 6 was dissolved in tetrahydrofuran, and was cast on a glass plate. After removal of tetrahydrofuran by slow evaporation in a refrigerator, the glass plate was heated at 50° C. for 24 h. The resulting cured material on the glass plate was insoluble in general organic solvents such as tetrahydrofuran, chloroform, and dimethylformamide, indicating that the condensation reaction of siloxy group resulted in curing reaction of 6. It can be considered that the formed cured material would be covalently bonded with the glass surface by the reaction of siloxy group with the glass surface. A similar treatment of 7 gave the similar coating material insoluble in tetrahydrofuran, chloroform, and dimethylformamide. In Table 1, thermal properties of the formed coating material are shown. The coating material comprises thiol groups, which can further react with epoxides, isocyanates, and any other thiol reactive groups for further modification of the coating material.

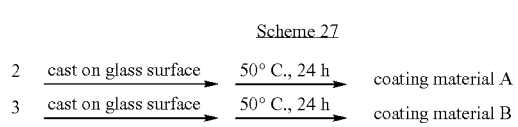

TABLE 1

Thermal properties of the cured materials

| run | coating | tem. of weight loss (° C.) 5% | 10% | $T_g$ (° C.) |
|---|---|---|---|---|
| 1 | A | 174 | 233 | 14 |
| 2 | B | 207 | 239 | 24 |

Coating with Jeffamine® Modified cycDTC-Si in Combination with Epoxides

1$^{st}$ Step: Reaction Between Modified Jeffamine® 7 and Epoxide

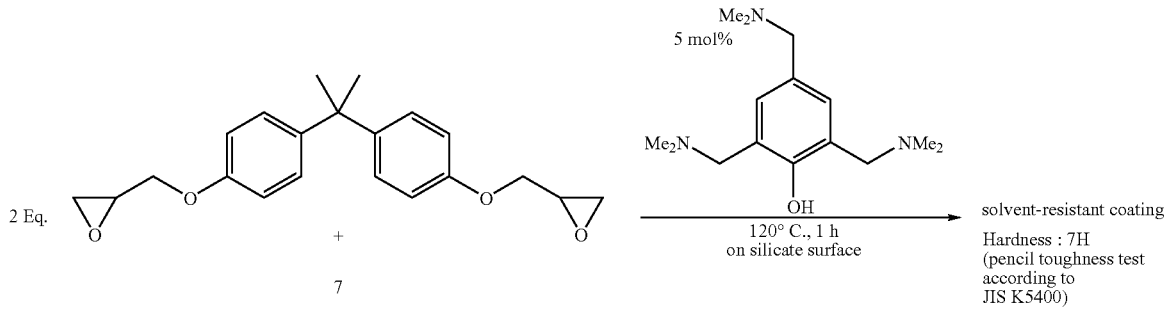

To the modified Jeffamine® 7 (shown in Scheme 28) prepared from Jeffamine® ($M_n$=400) (0.574 g, 1.44 mmol) and DTC-Si (0.918 g, 2.94 mmol), bisphenol A diglycidyl ether (1.023 g, 3.01 mmol) and 2,4,6-tris(dimethylaminomethyl) phenol (0.0320 g, 0.121 mmol) were added. The resulting mixture was stirred at room temperature for 1 hour.

2$^{nd}$ Step: Coating of a Glass Surface by Curing Reaction of the Epoxy Resin Product Obtained on the 1$^{st}$ Step The mixture from the 1$^{st}$ step was cast on a glass surface, and cured at 120° C. for 1 hour. The resulting cured resin was insoluble in general organic solvents and water. Mechanical toughness of the layer was tested by pencil toughness test according to the procedure for JIS-K5400, to find that its toughness was graded as 7H.

Further Surface Modifications of Silicate Surfaces with Monomeric cycDTC-Si or Its Corresponding Soluble Oligomers 1$^{st}$ Step: Coating (Pretreatment) of a Silicate Surface with cycDTC-Si

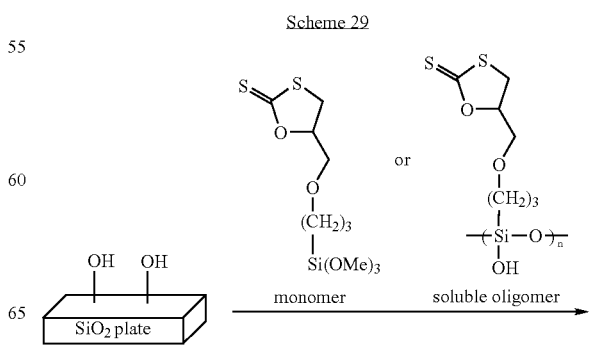

-continued

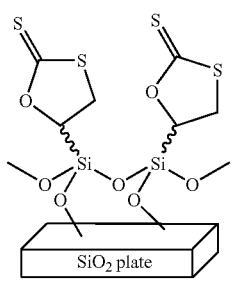

CycDTC-Si or its soluble oligomers can be used as reagents for coating (or pretreatment) of silicate (glass or quartz) surfaces.

Example I (coating): To cycDTC-Si (1004 mg, 3.21 mmol), water (87.0 mg, 4.83 mmol) and triethylamine (174 mg, 0.172 mmol) were added at room temperature. After the resulting mixture was stirred at room temperature for 5 hours, the volatile fractions were removed under reduced pressure. Then, the residue (=soluble oligomer) was dissolved in THF (5 ml) and was cast on a quartz plate or a glass plate. After removal of THF by slow evaporation, the quartz or the glass plate was heated at 50° C. to 80° C. for 24 hours, to obtain the corresponding plate, coated with a polysiloxane layer having a cycDTC moiety.

Example II (surface pretreatment): To a THF solution (10 ml) of cycDTC-Si (1004 mg, 3.21 mmol), water (87.0 mg, 4.83 mmol) and triethylamine (174 mg, 0.172 mmol) were added at room temperature. To the resulting solution, a quartz or a glass plate was immersed for 24 h at room temperature and was rinsed with THF twice. The plate was heated at 50° C. for 24 hours, to obtain the corresponding plate pretreated with a polysiloxane layer having a cycDTC moiety.

The coated or pretreated plates have a DTC moiety on their surface and thus they have a reactive surface which can be modified as follows.

$2^{nd}$ Step: Reaction of the Coated (Pretreated) Surfaces with Amine

The cycDTC moiety on the glass or quartz plate readily reacts with amines. The resulting surface has SH groups due to the reaction of cycDTC with the amine. This SH group can be further reacted with electrophiles such as isocyanate and epoxide.

Example I: The cycDTC-coated glass was immersed into a THF solution (50 ml) of diethylamine (5 ml) to convert the cycDTC moiety into the corresponding adduct having a SH group. The SH group in the coated layer was treated with n-propyl isocyanate (5 ml) or phenyl isocyanate (5 ml) to cap the SH group. The resulting coating layer was insoluble in organic solvents such as THF, DMF, and chloroform. The mechanical toughness of the coated layers was tested by pencil toughness test (JIS-K5400), to find that its toughness was graded as less than 6B.

Example II: The DTC-coated glass was immersed into a THF solution (50 ml) of diethylamine (5 ml) to convert the cycDTC moiety into the corresponding adduct having a SH group. The SH group in the coated layer was treated with 2,2-bis(4-glycidoxyphenyl)propane (1407 mg, 4.13 mmol) in the presence of 2,4,6-tris(dimethyl-aminomethyl)phenol (53.0 mg, 0.200 mmol) at 120° C. for 1 hour. The obtained coating layer was insoluble in organic solvents such as THF, DMF, and chloroform. The pencil toughness was graded as 4H.

Example III: When the substrate is quartz, the reactions above can be monitored with UV-Vis spectroscopy. cycDTC has a strong absorption, whose maximum intensity is in a range of 280 to 300 nm. After the treatment with amine, this absorption disappears.

Scheme 30

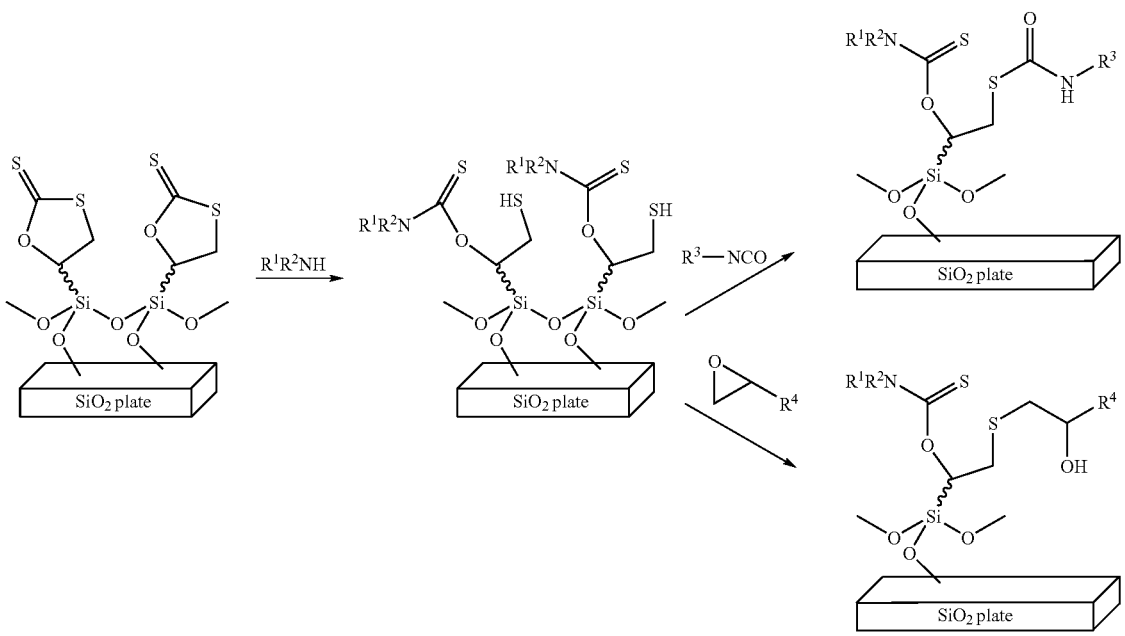

Further Surface Modifications of Silicate Surfaces with a Cationically Copolymerized Copolymer Made of cycDTC-Si and cycDTC-OPh (Synthesis is Described Above)

Scheme 31

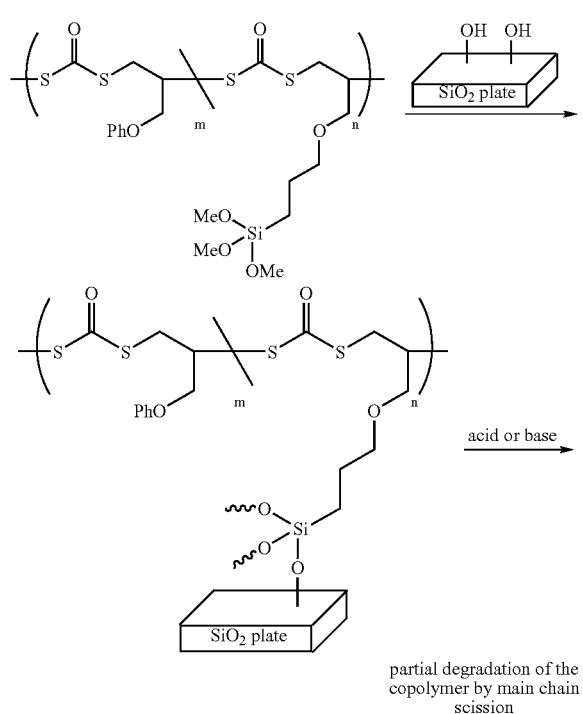

partial degradation of the copolymer by main chain scission $1^{st}$ Step: Coating (Pretreatment) of Silicate Surfaces by the Copolymer The copolymer was dissolved in THF (7 ml), and was cast on a glass plate (1.5 cm×4 cm). The glass plate was heated at 50° C., for 24 hours, to obtain the corresponding glass plate permanently coated with the copolymer. The coating layer was insoluble in organic solvents such as THF, DMF, and chloroform. Mechanical toughness of the both layers was tested by pencil toughness test according to the procedure for JIS-K5400, to find that its toughness was graded as 4B.

$2^{nd}$ Step:

The coated glass plate was immersed in a dichloromethane solution of trifluoromethane sulfonic acid (1M) at ambient temperature for 24 h. The copolymer layer was gradually degraded and a mixture of oligomers was found in the dichloromethane solution (by NMR and SEC). Such degradation occurred when the coated glass plate was treated with a refluxing THF solution of benzylamine (1M) for 24 h.

Coating and Bonding of Titanium Alloys $1^{st}$ Step: Preparation of Sol-gel Primers for the Application on Titanium Alloy Specimens Example 1a 1. 500 ml water were placed in a 1000 ml flask and the pH value was adjusted to 7-8. Under stirring 46.02 g of 5-(3-trimethoxysilylpropyloxymethyl)-1,3-oxathiolane-2-thione (1a) were added and the mixture was allowed to swell for 30 minutes.
2. 7.3 ml glacial acetic acid and 10 ml of a 70% solution (w/v) of zirconium(IV)propylate were diluted with 17 ml of de-ionized water under stirring. Subsequently, 300 ml of de-ionized water were added under stirring and the pH value was adjusted to be about 5.
3. The mixture obtained in step 2. was added to the mixture obtained in step 1. under stirring. Subsequently the flask used in step 2. was washed with 200 ml of de-ionized water, which was afterwards added to the combined mixtures. The resulting mixture was allowed to stand for 30 minutes.

Example 1b

The preparation was performed in the same manner as described for Example 1a, except for replacing 46.02 g 5-(3-trimethoxysilylpropyloxymethyl)-1,3-oxathiolane-2-thione by a mixture of 23.0 g 5-(3-trimethoxysilylpropyloxymethyl)-1,3-oxathiolane-2-thione and 18.2 g (3-glycidoxypropyl)trimethoxysilane.

Comparative Example 1

The preparation was performed in the same manner as described for Example 1a, except for replacing the 5-(3-trimethoxysilylpropyloxymethyl)-1,3-oxathiolane-2-thione (1a) by 34 ml (3-glycidoxypropyl)trimethoxysilane.

$2^{nd}$ Step: Pre-Treatment of Titanium Alloy Specimens for Immersion Tests

Cleaning of Titanium Alloy Specimens (Ti6Al4V)

For the experiments titanium tensile shear specimens of the following dimensions 100×25×1.6 mm were used.

First the titanium alloy specimens were submerged in a 500 g/l solution of Turco® 5578 in water (an alkaline cleaning agent obtainable from Henkel Corporation; the above concentration corresponds to approximately 50% (w/v) of an alkali hydroxide) at a temperature of 95° C. for 5 minutes. Next the titanium alloy specimens were rinsed with de-ionized water for 2 minutes.

$3^{rd}$ Step: Applying the Sol-Gel Formulations of Examples 1a, 1b and Comparative Example 1 onto Titanium Alloy Specimens The titanium alloy sheets were submerged in the sol-gel of Examples 1a, 1b and Comparative Example 1, respectively, for two minutes at room temperature while stirring. Subsequently the excessive sol-gel was allowed to drain for 5 seconds. The specimens were dried for 30 minutes at 60° C. in an air-circulating oven. In addition to the thus primed specimens titanium alloy specimens which were not subjected to sol-gel priming were used as a further control example. Table 2 gives an overview of the different pre-treatment procedures.

TABLE 2

| specimen | pre-treatment procedure |
| --- | --- |
| A | only cleaning steps |
| B | cleaning steps plus pre-treatment with sol-gel of Example 1a |
| C | cleaning steps plus pre-treatment with sol-gel of Example 1b |
| D | cleaning steps plus pre-treatment with sol-gel of Comparative Example 1 |

$4^{th}$ Step: Bonding of Pre-treated Titanium Alloy Specimens

To join the specimens A, B and D, the film adhesive Loctite® EA 9696 (Henkel KGaA, Duesseldorf, Germany) was used. Curing of the adhesive was performed at 120° C. for 90 minutes. Those joined specimens were tested in immersion test I.

To join specimens A, B and C, the adhesive Terokal® 5070 MB-25—an epoxy resin adhesive based on bisphenol A—(obtainable from Henkel Teroson GmbH, Heidelberg, Germany) was used. Curing of the adhesive was performed at 170° C. for 30 minutes. These joined specimens were tested in immersion test II.

Immersion Test I

Determination of Aging at 60° C.—Loctite® EA 9696 Bonded Specimens

To determine aging the joined composites from specimens A, B and D were submerged in de-ionized water at 60° C. and stored for different periods of time, i.e., 0, 720 and 1440 hours, respectively. The results of the immersion test are shown in Table 3.

TABLE 3

| | Immersion at 60° C. (immersion test I) in hours | | | | | |
|---|---|---|---|---|---|---|
| | 0 | | 720 | | 1440 | |
| Specimen | TSS [MPa] | FP [% cf] | TSS [MPa] | FP [% cf] | TSS [MPa] | FP [% cf] |
| A | 39.5 | 100 | 14.6 | 0 | 13.6 | 0 |
| B | >40 | 100 | 25.9 | 90 | 21.8 | 80 |
| D | 39.3 | 100 | 21.9 | 0 | 19.0 | 0 |

TSS: tensile shear strength
FP: fracture pattern

Specimen A, corresponding to the cleaning pre-treatment only, shows inferior results for tensile shear strength and fracture pattern at 720 and 1440 hours compared to sol-gel pre-treated specimens B and D. The results unambiguously show that the sol-gel, which is prepared using a cyclic dithiocarbonate of the invention (sol-gel B), mediates a significant increase in adhesion properties in the bonding/immersion test. Further the enhanced tensile shear strength and improved fracture pattern clearly shows that sol-gel from Example 1a based on the compounds of the invention acts as superior primer for titanium alloy surfaces even under storage conditions in a humid and warm environment.

Immersion Test II

Determination of Aging at 70° C.—Terokal® 5070 MB-25 Bonded Specimens

To determine aging the joined composites from specimens A, C and D were submerged in de-ionized water at 70° C. and stored for different periods of time, i.e., 0, 21, 42 and 63 days, respectively. The results of the immersion test are shown in Table 4.

Specimen A (cleaning pre-treatment only) shows inferior long-term characteristics for tensile shear strength and fracture pattern compared to sol-gel pre-treated specimens C and D. The difference between specimens C and D is still remarkable but smaller than in immersion test I. This seems to be due to the use of a combination of both 5-(3-trimethoxysilylpropyloxymethyl)-1,3-oxathiolane-2-thione and 18.2 g (3-glycidoxy-propyl)trimethoxysilane in the pre-treatment of specimen C.

Coating and Bonding of Aluminum Alloys $1^{st}$ Step: Preparation of Sol-Gel Primers for the Application on Aluminum Alloy Specimens Example 2

1. 500 ml water were placed in a 1000 ml flask and the pH value was adjusted to 7-8. Under stirring 23.0 g 5-(3-trimethoxysilylpropyloxymethyl)-1,3-oxathiolane-2-thione (1a) and 18.2 g (3-glycidoxypropyl)trimethoxysilane were added and the mixture was allowed to swell for 30 minutes.
2. 7.3 ml glacial acetic acid and 10 ml of a 70% solution (w/v) of zirconium(IV)propylate were diluted with 17 ml of de-ionized water under stirring. Subsequently 300 ml of de-ionized water were added under stirring and the pH value was adjusted to be about 5.
3. The mixture obtained in step 2. was added to the mixture obtained in step 1. under stirring. Subsequently the flask used in step 2. was washed with 200 ml of de-ionized water, which was afterwards added to the combined mixtures. The resulting mixture was allowed to stand for 30 minutes.

Comparative Example 2

The preparation was performed in the same manner as described for the Example 2, except for replacing 23.0 g 5-(3-trimethoxysilylpropyloxymethyl)-1,3-oxathiolane-2-thione and 18.2 g (3-glycidoxypropyl)trimethoxysilane by 34 ml (3-glycidoxypropyl)trimethoxysilane.

$2^{nd}$ Step: Pre-Treatment of Aluminum Specimens for Immersion Tests

Cleaning of Aluminum Specimens (Aluminum 6016 and Aluminum 2024)

In a first step the aluminum specimens were submerged in a 6% solution of Ridoline® 1580 in water (an alkaline degreasing agent obtainable from Henkel KGaA, Duesseldorf, Germany) at a temperature of 60° C. for 5 minutes. In a second step the aluminum specimens were rinsed twice with water for 2 minutes.

TABLE 4

| | Immersion at 70° C. (immersion test II) in days | | | | | | | |
|---|---|---|---|---|---|---|---|---|
| | 0 | | 21 | | 42 | | 63 | |
| Specimen | TSS [MPa] | FP [% cf] | TSS [MPa] | FP [% cf] | TSS [MPa] | FP [% cf] | TSS [MPa] | FP [% cf] |
| A | 29.6 | 100 | 12.5 | 60 | 5.7 | 0 | 4.3 | 0 |
| C | 31.8 | 90 | 18.5 | 100 | 18.4 | 95 | 17 | 95 |
| D | 23.2 | 90 | 18.5 | 95 | 17.1 | 95 | 14.9 | 95 |

TSS: tensile shear strength
FP: fracture pattern
% cf: % cohesive failure

Deoxidizing of Aluminum Specimens

Aluminum 6016 specimens were deoxidized with a 1% solution of Deoxidizer 4902 (deoxidizer on the basis of sulfuric acid and ammonia bifluoride; Henkel KGaA, Duesseldorf, Germany) at room temperature for 2 minutes and subsequently rinsed twice with distilled water.

Aluminum 2024 specimens were deoxidized with a 15% solution of nitric acid at room temperature by a 5-second-pickling procedure and subsequently rinsed twice with distilled water.

$3^{rd}$ Step: Applying the Sol-gel Formulations of Example 2 and Comparative Example 2 on Aluminum Specimens The cleaned and deoxidized aluminum sheets were submerged in the sol-gel of Example 2 and Comparative Example 2, respectively, for two minutes at room temperature while stirring. Subsequently the excessive sol-gel was allowed to drain for 5 seconds. The specimens were dried for 30 minutes at 60° C. in an air-circulating oven. Table 5 gives an overview of the different pre-treatment procedures.

TABLE 5

| specimen | pre-treatment procedure |
| --- | --- |
| E | only cleaning steps |
| F | cleaning steps plus pre-treatment with sol-gel of Example 2 |
| G | cleaning steps plus pre-treatment with sol-gel of Comparative Example 2 |

$4^{th}$ Step: Bonding of Pre-treated Aluminum Specimens

To join specimens A, B and C, the adhesive Terokal® 5070 MB-25—an epoxy resin adhesive based on bisphenol A—(obtainable from Henkel Teroson GmbH, Heidelberg, Germany) was used. Curing of the adhesive was performed at 170° C. for 30 minutes. The joined specimens were tested under the conditions of the above immersion test II.

Immersion Test II

Determination of Aging at 70° C.—Terokal-5070 MB-25 Bonded Specimens

To determine aging, the joined composites from specimens E, F and G were submerged in de-ionized water at 70° C. and stored for different periods of time, i.e., 0, 21, 42 and 63 days, respectively. The results of the immersion test are shown in Table 6.

Specimen A (cleaning pre-treatment only), shows inferior long-term characteristics for tensile shear strength and fracture pattern compared to sol-gel pre-treated specimens C and D. The difference between specimens C and D is still remarkable but smaller than in immersion test I. This seems to be due to the use of a combination of both 5-(3-trimethoxysilylpropyloxymethyl)-1,3-oxathiolane-2-thione and 18.2 g (3-glycidoxy-propyl)trimethoxysilane in the pre-treatment of specimen C.

Use of the Cyclic Dithiocarbonates of the Invention as Adhesion Promoters in Adhesives An aluminum substrate (Al 6016; 100×25×0.8 mm) was pre-treated with Alodine® 2040 (a chrome-free passivate based on hexafluorotitanic acid obtainable from Henkel KGaA, Duesseldorf Germany). The aluminum substrates were bonded together with a base formulation lacking the compounds of the invention and an adhesive formulation containing compound 1a. The curing conditions comprised heating to 120° C. for 60 minutes. Subsequently aging was investigated in a cata-plasma test as described in the following. Bonded composites were wrapped in absorbent cotton which was wetted with de-ionized water. Afterwards the cotton-wrapped composites were further wrapped in aluminum foil and welded into polyethylene foil. The thus-wrapped specimen was stored at 70° C. for 168 and 336 hours, respectively. After aging in humid conditions, cold storage at −25° C. for 16 hours was performed. The bonded composites were unwrapped at room temperature and tested for tensile shear strength. The results are summarized in Table 7:

TABLE 7

| | tensile shear strength [MPa] | |
| --- | --- | --- |
| aging under cataplasma conditions in days | base formulation (comparative) | adhesive formulation (according to invention) |
| 0 | 18.3 | 16.2 |
| 7 | 9.9 | 14.4 |
| 14 | 9.6 | 13.7 |

| base formulation: | | adhesive formulation containing compound 1a: | |
| --- | --- | --- | --- |
| 62.2% | DER 331P (Dow) | 60.3% | DER 331P (Dow) |
| 37.8% | Jeffamine ® D400 (Huntsman) | 34.7% | Jeffamine ® D400 (Huntsman) |
| | | 5.0% | compound 1a |

DER 331P: epoxy resin based on bisphenol A diglycidyl ether

TABLE 6

| | Immersion at 70° C. (immersion test II) in days | | | | | | | |
| --- | --- | --- | --- | --- | --- | --- | --- | --- |
| | 0 | | 21 | | 42 | | 63 | |
| Specimen | TSS [MPa] | FP [% cf] | TSS [MPa] | FP [% cf] | TSS [MPa] | FP [% cf] | TSS [MPa] | FP [% cf] |
| aluminum 6016 | | | | | | | | |
| E | 18.3 | 90 | 2.7 | 0 | 2.1 | 0 | 1.1 | 0 |
| F | 18.9 | 90 | 16.4 | 95 | 14.9 | 95 | 13.7 | 95 |
| G | 18.9 | 90 | 16.0 | 90 | 14.8 | 95 | 13.1 | 95 |
| aluminum 2024 | | | | | | | | |
| E | 30.4 | 100 | 10.2 | 30 | 5.1 | 0 | 2.2 | 0 |
| F | 31.3 | 90 | 19.4 | 95 | 16.4 | 95 | 15.2 | 95 |
| G | 25.6 | 90 | 18.2 | 95 | 16.0 | 95 | 14.2 | 95 |

TSS: tensile shear strength
FP: fracture pattern

Use of the Liquid Oligomer as an Additive for Epoxy-Amine Curing Reaction

Bisphenol A-diglycidylether (0.023 g) and the liquid oligomer ($M_n$=560, PDI=2.06; 0.260 g) described in the preparative section were mixed with stirring under evacuation. To this mixture, Jeffamine® (pre-cooled at 0° C.; 0.786 g) was added and the mixture was mixed with degassing under vaccum below 15° C. for 30 min. The obtained mixture was transferred into a 1 ml volume measuring flask. [0141] Based on the weight of 1 ml of the mixture, the density of the epoxy formulation before curing was calculated. Then, 1.61 g of the mixture was transferred into a silicon mold (6.0 mm by 60 mm by 70 mm), and was cured at 120° C. for 1 h, to obtain 1.59 g of the plate-shaped cured resin. Its density was measured by electronic densimeter. Based on the density values, the degree of volume change was calculated to be −4.4%, according to the equation $(D_{before\ curing})/(D_{after\ curing})-1$. The volume change observed for the reference experiment in the absence of the liquid oligomer was −6.1%. The following Scheme 32 serves to illustrate this experiment:

What is claimed is:

1. A 1,3-oxathiolane-2-thione compound of formula (I)

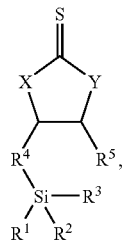

wherein: $R^1$, $R^2$, and $R^3$ are the same or different, each of which denotes a straight-chain or branched alkoxy group with 1 to 6 carbon atoms; $R^4$ is a bridging group selected from the group consisting of unsubstituted aliphatic and unsubstituted heteroaliphatic group, $R^5$ is hydrogen, X is S, and Y is O.

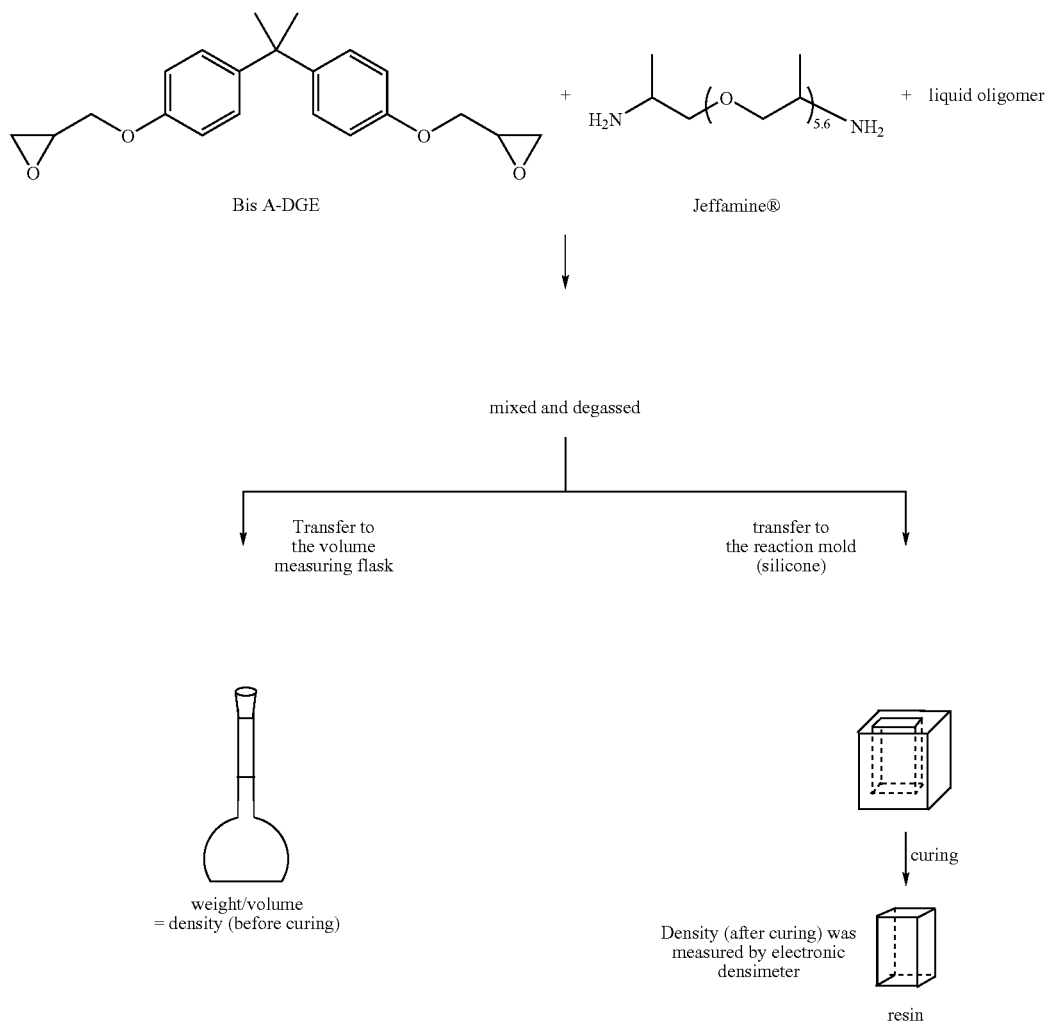

2. The 1,3-oxathiolane-2-thione compound according to claim 1, wherein $R^1$ $R^2$ and $R^3$ are the same or different, each of which denotes a straight-chain or branched alkoxy group with 1 to 4 carbon atoms.

3. The 1,3-oxathiolane-2-thione compound according to claim 1, wherein $R^1$ $R^2$ and $R^3$ are the same or different, each of which denotes a methoxy or ethoxy group.

4. The 1,3-oxathiolane-2-thione compound according to claim 1, wherein $R_4$ is

—$(CH_2)_3OCH_2$—.

* * * * *